US008647754B2

(12) United States Patent
Mizuki et al.

(10) Patent No.: US 8,647,754 B2
(45) Date of Patent: Feb. 11, 2014

(54) AROMATIC DIAMINE DERIVATIVE AND ORGANIC ELECTROLUMINESCENT DEVICE USING THE SAME

(75) Inventors: Yumiko Mizuki, Sodegaura (JP); Masakazu Funahashi, Sodegaura (JP); Masahiro Kawamura, Sodegaura (JP); Mitsunori Ito, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 349 days.

(21) Appl. No.: 12/810,709

(22) PCT Filed: Dec. 25, 2008

(86) PCT No.: PCT/JP2008/073593
§ 371 (c)(1),
(2), (4) Date: Sep. 9, 2010

(87) PCT Pub. No.: WO2009/084585
PCT Pub. Date: Jul. 9, 2009

(65) Prior Publication Data
US 2011/0006289 A1     Jan. 13, 2011

(30) Foreign Application Priority Data

Dec. 28, 2007  (JP) ................................. 2007-340952

(51) Int. Cl.
*H01L 51/50*  (2006.01)

(52) U.S. Cl.
USPC ............ 428/690; 428/917; 313/504; 313/506

(58) Field of Classification Search
None
See application file for complete search history.

(56) References Cited

U.S. PATENT DOCUMENTS

| | | | |
|---|---|---|---|
| 5,536,949 A | 7/1996 | Hosokawa et al. | |
| 5,635,308 A | 6/1997 | Inoue et al. | |
| 7,425,653 B2 * | 9/2008 | Funahashi | 564/434 |
| 7,524,568 B2 * | 4/2009 | Funahashi | 428/690 |
| 7,816,017 B2 * | 10/2010 | Funahashi et al. | 428/690 |
| 8,058,478 B2 * | 11/2011 | Funahashi et al. | 564/426 |
| 8,173,272 B2 * | 5/2012 | Jang et al. | 428/690 |
| 2002/0048688 A1 | 4/2002 | Fukuoka et al. | |
| 2003/0157364 A1 | 8/2003 | Senoo et al. | |
| 2006/0052641 A1 | 3/2006 | Funahashi | |
| 2006/0152146 A1 * | 7/2006 | Funahashi | 313/504 |
| 2006/0210830 A1 * | 9/2006 | Funahashi et al. | 428/690 |
| 2007/0114917 A1 | 5/2007 | Funahashi et al. | |
| 2007/0278938 A1 | 12/2007 | Yabunouchi et al. | |
| 2008/0100207 A1 * | 5/2008 | Park et al. | 313/504 |
| 2008/0102311 A1 | 5/2008 | Funahashi | |
| 2008/0203905 A1 | 8/2008 | Je et al. | |
| 2009/0134781 A1 | 5/2009 | Jang et al. | |

FOREIGN PATENT DOCUMENTS

| | | |
|---|---|---|
| JP | 11 3782 | 1/1999 |
| JP | 2007 137837 | 6/2007 |
| JP | 2008 214332 | 9/2008 |
| WO | 2007 105917 | 9/2007 |
| WO | 2007 108666 | 9/2007 |
| WO | 2008 016018 | 2/2008 |

OTHER PUBLICATIONS

U.S. Appl. No. 12/854,247, filed Aug. 11, 2010, Funahashi, et al.

* cited by examiner

*Primary Examiner* — Dawn L. Garrett
(74) *Attorney, Agent, or Firm* — Oblon, Spivak, McClelland, Maier & Neustadt, L.L.P.

(57) ABSTRACT

Disclosed is an aromatic diamine derivative represented by the following general formula (I), which has a chrysene structure in which a phenyl group having a substituted or unsubstituted silyl group is a substituent for an amino group. Also disclosed is an organic electroluminescence device including an organic thin film layer formed of one or more layers including at least a light emitting layer and interposed between a cathode and an anode, in which at least one layer of the organic thin film layer contains the aromatic diamine derivative by itself or as a component of a mixture, the device having a long lifetime and high luminous efficiency. (In the formula, $R^1$ to $R^{10}$ each independently represent a hydrogen atom, an alkyl group having 1 to 50 carbon atoms, or the like, and $R^{11}$ represents a substituted or unsubstituted alkyl group having 1 to 50 carbon atoms or the like, and at least one of A, B, and C represents a substituted or unsubstituted silyl group, and the others each represent a hydrogen atom, a substituted or unsubstituted alkyl group having 1 to 50 carbon atoms, or the like, a, b, c, and d each independently represent an integer of 1 to 5.)

10 Claims, No Drawings

AROMATIC DIAMINE DERIVATIVE AND ORGANIC ELECTROLUMINESCENT DEVICE USING THE SAME

CROSS-REFERENCE TO RELATED APPLICATIONS

This application is a National Stage of PCT/JP08/073593 filed Dec. 25, 2008 and claims the benefit of JP 2007-340952 filed Dec. 28, 2007.

TECHNICAL FIELD

The present invention relates to an aromatic diamine derivative and an organic electroluminescence device using the same, in particular, an organic electroluminescence device having a long lifetime and high luminous efficiency, and an aromatic diamine derivative for realizing the device.

BACKGROUND ART

A large number of organic electroluminescence (EL) devices each using an organic substance have been developed because of their potential to find applications in solid light emission type, inexpensive, large-area, full-color display devices. In general, an organic EL device is constituted of a light emitting layer and a pair of opposing electrodes between which the layer is interposed. Light emission is the phenomenon in which when an electric field is applied between both the electrodes, an electron is injected from a cathode side and a hole is injected from an anode side, and, further, the electron recombines with the hole in the light emitting layer to produce an excited state, and energy generated upon return of the excited state to a ground state is emitted as light.

A conventional organic EL device was driven at a voltage higher than the voltage at which an inorganic light emitting diode is driven, and had emission luminance and luminous efficiency lower than those of the diode. In addition, the properties of the device deteriorated remarkably, so the device has not been put into practical use. A recent organic EL device has been gradually improved, but actually, additionally high luminous efficiency and an additionally long lifetime of the device are still requested.

As a conventional organic light emitting material, for example, a single monoanthracene compound (see Patent Document 1) and a single bisanthracene compound (see Patent Document 2) are disclosed. In addition, a technique for a long-lifetime organic EL device obtained by adding, for example, styrylamine to a distyryl compound to be used as an organic light emitting material is proposed (see Patent Document 3).

In addition, a technique involving the use of each of a monoanthracene or bisanthracene compound and a distyryl compound in an organic light emitting medium layer is disclosed (see Patent Document 4).

Further, a blue light emitting device using a diaminochrysene derivative is disclosed (see Patent Document 5). In addition, an invention in which an aromatic amine derivative having an arylene group at its center is used as a hole transporting material (see Patent Document 6), an invention in which an aromatic amine derivative where a dibenzofuran ring, a dibenzothiophene ring, a benzofuran ring, a benzothiophene ring, or the like is bonded to a nitrogen atom through an arylene group is used as a hole transporting material (see Patent Document 7), and the like are also disclosed. In addition, an invention in which an aromatic diamine derivative where a phenyl group having a substituted or unsubstituted silyl group substitutes for a nitrogen atom is used as a material for a light emitting layer (see Patent Document 8) is disclosed.

Patent Document 1: JP 11-3782 A
Patent Document 2: JP 08-12600 A
Patent Document 3: WO 94/006157 A1
Patent Document 4: JP 2001-284050 A
Patent Document 5: WO 04/044088 A1
Patent Document 6: JP 3508984 B2
Patent Document 7: WO 07/125,714 A1
Patent Document 8: WO 07/108,666 A1

DISCLOSURE OF THE INVENTION

Problems to be Solved by the Invention

The organic light emitting material described in Patent Document 1 is not practical because of, for example, the following reasons. The material provides a luminance of only 1650 $cd/m^2$ at a current density of 165 $mA/cm^2$, and its efficiency is 1 cd/A, which is an extremely low value. In addition, the organic light emitting material described in Patent Document 2 must also be additionally improved so as to be put into practical use because its efficiency is as low as about 1 to 3 cd/A. The method described in Patent Document 3 is still susceptible to improvement because even the lifetime obtained by the method is not long enough for practical applications. The technique described in Patent Document 4 involves the following problem. That is, an emission spectrum shifts to longer wavelengths owing to the conjugate structure of the styryl compound, and hence the resultant color purity is poor. Although the device described in Patent Document 5 is excellent in luminous efficiency, its lifetime is still insufficient, and an additional improvement has been requested. In addition, additional improvements in lifetime and luminous efficiency have also been requested of each of the devices described in Patent Documents 6 to 8.

The present invention has been made to solve such problems, and an object of the present invention is to provide an organic EL device having a long lifetime and high luminous efficiency, and a compound that realizes the device.

Means for Solving the Problems

The inventors of the present invention have made extensive studies to achieve the object. As a result, the inventors have found that the use of an aromatic amine derivative having a special structure obtained by using a phenyl group having a substituted or unsubstituted silyl group as a substituent for an amino group in an aromatic diamine derivative having a chrysene structure as a light emitting material provides high luminous efficiency and a long lifetime. The present invention has been completed on the basis of such finding.

That is, the present invention provides an aromatic diamine derivative represented by the following general formula (I):

[Chem 1]

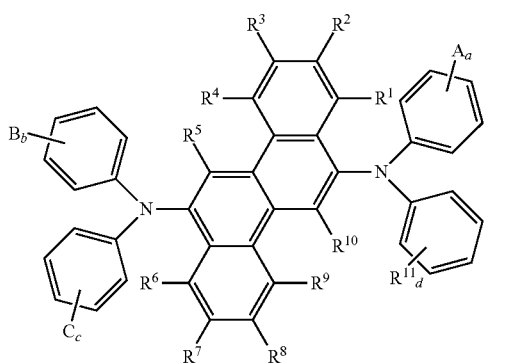

(I)

where:
$R^1$ to $R^{10}$ each independently represent a hydrogen atom, an alkyl group having 1 to 50 carbon atoms, a cycloalkyl group having 3 to 50 carbon atoms, an aralkyl group having 7 to 50 carbon atoms, or an aryl group having 6 to 50 carbon atoms, and $R^{11}$ represents a substituted or unsubstituted alkyl group having 1 to 50 carbon atoms, a substituted or unsubstituted cycloalkyl group having 3 to 50 carbon atoms, a substituted or unsubstituted aralkyl group having 7 to 50 carbon atoms, a substituted or unsubstituted alkyloxy group having 1 to 50 carbon atoms, or a substituted or unsubstituted aryl group having 6 to 50 carbon atoms; and at least one of A, B, and C represents a substituted or unsubstituted silyl group, and the others each represent a hydrogen atom, a substituted or unsubstituted alkyl group having 1 to 50 carbon atoms, a substituted or unsubstituted cycloalkyl group having 3 to 50 carbon atoms, a substituted or unsubstituted aralkyl group having 7 to 50 carbon atoms, a substituted or unsubstituted alkyloxy group having 1 to 50 carbon atoms, or a substituted or unsubstituted aryl group having 6 to 50 carbon atoms, a, b, c, and d each independently represent an integer of 1 to 5, and when a, b, c, or d represents an integer of 2 to 5, A's, B's, C's, or $R^{11}$'s may represent groups identical to or different from each other on the same benzene ring, provided that when B and C each represent a trimethylsilyl group, b and c each represent 1, and B and C each substitute at a para position, and when A and $R^{11}$ each represent a methyl group, a structure in which a and d simultaneously represent 1, and A and $R^{11}$ each substitute at a para position is excluded, and when A represents a trimethylsilyl group, a represents 1, and A substitutes at a para position, and when $R^{11}$ represents a methyl group, d represents 2, and the two $R^{11}$'s each substitute at a meta position, a structure in which B represents a trimethylsilyl group, b represents 1, B substitutes at a para position, C represents a methyl group, c represents 2, and the two C's each substitute at a meta position is excluded.

In addition, the present invention provides an organic EL device including an organic thin film layer formed of one or more layers including at least a light emitting layer and interposed between a cathode and an anode, in which at least one layer of the organic thin film layer contains the aromatic diamine derivative by itself or as a component of a mixture.

Effects of the Invention

The use of the aromatic diamine derivative of the present invention as a material for an organic electroluminescence device stabilizes the nature of an organic electroluminescence device film and improves film formability. Further, in addition to the advantages, an organic EL device using the aromatic diamine derivative has high luminous efficiency, and hardly deteriorates even when used for a long time period, i.e., has a long lifetime while maintaining its blue color purity.

BEST MODE FOR CARRYING OUT THE INVENTION

An aromatic amine derivative of the present invention is an aromatic diamine derivative represented by the following general formula (I).

[Chem 2]

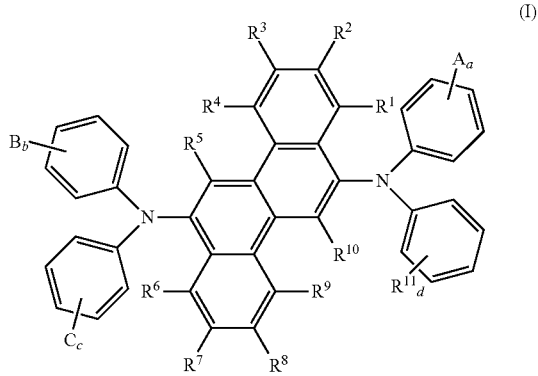

(I)

In the general formula (I), $R^1$ to $R^{10}$ each independently represent a hydrogen atom, an alkyl group having 1 to 50 carbon atoms, a cycloalkyl group having 3 to 50 carbon atoms, an aralkyl group having 7 to 50 carbon atoms, or an aryl group having 6 to 50 carbon atoms. It should be noted that, in the description, the number of carbon atoms of each group in a general formula represents a number excluding the number of carbon atoms of a substituent.

Examples of the alkyl group having 1 to 50 carbon atoms include a methyl group, an ethyl group, an n-propyl group, an isopropyl group, an n-butyl group, an isobutyl group, an s-butyl group, a t-butyl group, and various pentyl groups (the term "various" means that all of linear, branched, and cyclic groups are included, and the same holds true for the following). Of those, an alkyl group having 1 to 10 carbon atoms is preferred.

Examples of the cycloalkyl group having 3 to 50 carbon atoms include a cyclopropyl group, a cyclopentyl group, a cyclohexyl group, a 4-methylcyclohexyl group, and a cyclooctyl group. Of those, a cyclohexyl group having 5 to 8 carbon atoms is preferred.

Examples of the aralkyl group having 7 to 50 carbon atoms include a benzyl group, an α,α-phenylmethylbenzyl group, an α,α-dimethylbenzyl group, an α-phenoxybenzyl group, an α,α-methylphenylbenzyl group, an α,α-ditrifluoromethylbenzyl group, a triphenylmethyl group, an α-benzyloxybenzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group. Of those, an aralkyl group having 7 to 20 carbon atoms is preferred.

Examples of the aryl group having 6 to 50 carbon atoms include a phenyl group, a tolyl group, a naphthyl group, an acenaphthylenyl group, an anthryl group, a phenanthryl group, a phenarenyl group, a fluorenyl group, an α-indacenyl group, and an as-indacenyl group. Of those, an aryl group having 6 to 14 carbon atoms is preferred.

In addition, in the general formula (I), at least one of A, B, and C represents a substituted or unsubstituted silyl group, and the others each represent a hydrogen atom, a substituted or unsubstituted alkyl group having 1 to 50 carbon atoms, a substituted or unsubstituted cycloalkyl group having 3 to 50 carbon atoms, a substituted or unsubstituted aralkyl group having 7 to 50 carbon atoms, a substituted or unsubstituted alkyloxy group having 1 to 50 carbon atoms, or a substituted or unsubstituted aryl group having 6 to 50 carbon atoms.

A substituent for the silyl group is, for example, an alkyl group having 1 to 20 carbon atoms, an aryl group having 6 to 14 carbon atoms, or an alkoxyl group having 1 to 20 carbon atoms. Examples of the alkyl group having 1 to 20 carbon atoms include a methyl group, an ethyl group, an n-propyl group, an isopropyl group, an n-butyl group, an isobutyl group, an s-butyl group, a t-butyl group, and various pentyl groups. Of those, an alkyl group having 1 to 5 carbon atoms is preferred. Examples of the aryl group having 6 to 14 carbon atoms include a phenyl group, a tolyl group, a naphthyl group, and an anthryl group. Of those, an aryl group having 6 to 10 carbon atoms is preferred. Examples of the alkoxyl group having 1 to 20 carbon atoms include a methoxy group, an ethoxy group, various propoxy groups, and various butoxy groups. Of those, an alkoxyl group having 1 to 5 carbon atoms is preferred.

In particular, the silyl group is more preferably a trialkylsilyl group, a dialkyl-monoarylsilyl group, a monoalkyl-diarylsilyl group, or a triarylsilyl group.

Examples of the substituted or unsubstituted alkyl group having 1 to 50 carbon atoms represented by any one of the remaining groups except the silyl group out of A, B, and C include a methyl group, an ethyl group, an n-propyl group, an isopropyl group, an n-butyl group, an isobutyl group, an s-butyl group, a t-butyl group, and various pentyl groups. Of those, an alkyl group having 1 to 10 carbon atoms is preferred.

Examples of the substituted or unsubstituted cycloalkyl group having 3 to 50 carbon atoms include a cyclopropyl group, a cyclopentyl group, a cyclohexyl group, a 4-methylcyclohexyl group, and a cyclooctyl group. Of those, a cyclohexyl group having 5 to 8 carbon atoms is preferred.

Examples of the substituted or unsubstituted aralkyl group having 7 to 50 carbon atoms include a benzyl group, an α,α-phenylmethylbenzyl group, an α,α-dimethylbenzyl group, an α-phenoxybenzyl group, an α,α-methylphenylbenzyl group, an α,α-ditrifluoromethylbenzyl group, a triphenylmethyl group, an α-benzyloxybenzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenyl isopropyl group, and a 1-chloro-2-phenylisopropyl group. Of those, an aralkyl group having 7 to 20 carbon atoms is preferred.

The substituted or unsubstituted alkyloxy group having 1 to 50 carbon atoms is a group represented by —OY, and examples of Y include the same alkyl groups as those exemplified for the "substituted or unsubstituted alkyl group having 1 to 50 carbon atoms represented by any one of the remaining groups except the silyl group out of A, B, and C" described above. Of those, an alkyl group having 1 to 10 carbon atoms is preferred, an alkyl group having 1 to 5 carbon atoms is more preferred, and a methyl group is still more preferred.

Examples of the substituted or unsubstituted aryl group having 6 to 50 carbon atoms include a phenyl group, a tolyl group, a methoxyphenyl group, an ethoxyphenyl group, a buthoxyphenyl group, a naphthyl group, an acenaphthylenyl group, an anthryl group, a phenanthryl group, a phenarenyl group, a fluorenyl group, an a-indacenyl group, and an as-indacenyl group.

$R^{11}$ represents a substituted or unsubstituted alkyl group having 1 to 50 carbon atoms, a substituted or unsubstituted cycloalkyl group having 3 to 50 carbon atoms, a substituted or unsubstituted aralkyl group having 7 to 50 carbon atoms, a substituted or unsubstituted alkyloxy group having 1 to 50 carbon atoms, or a substituted or unsubstituted aryl group having 6 to 50 carbon atoms.

Examples of such substituted or unsubstituted alkyl group having 1 to 50 carbon atoms include a methyl group, an ethyl group, an n-propyl group, an isopropyl group, an n-butyl group, an isobutyl group, an s-butyl group, a t-butyl group, and various pentyl groups. Of those, an alkyl group having 1 to 10 carbon atoms is preferred.

Examples of the substituted or unsubstituted cycloalkyl group having 3 to 50 carbon atoms include a cyclopropyl group, a cyclopentyl group, a cyclohexyl group, a 4-methylcyclohexyl group, and a cyclooctyl group. Of those, a cyclohexyl group having 5 to 8 carbon atoms is preferred.

Examples of the substituted or unsubstituted aralkyl group having 7 to 50 carbon atoms include a benzyl group, an α,α-phenylmethylbenzyl group, an α,α-dimethylbenzyl group, an α-phenoxybenzyl group, an α,α-methylphenylbenzyl group, an α,α-ditrifluoromethylbenzyl group, a triphenylmethyl group, an α-benzyloxybenzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenyl isopropyl group, and a 1-chloro-2-phenylisopropyl group. Of those, an aralkyl group having 7 to 20 carbon atoms is preferred.

The substituted or unsubstituted alkyloxy group having 1 to 50 carbon atoms is a group represented by —OY', and examples of Y' include the same alkyl groups as those exemplified for the "substituted or unsubstituted alkyl group having 1 to 50 carbon atoms represented by any one of the remaining groups except the silyl group out of A, B, and C" described above. Of those, an alkyl group having 1 to 10 carbon atoms is preferred, an alkyl group having 1 to 5 carbon atoms is more preferred, and a methyl group is still more preferred.

Examples of the substituted or unsubstituted aryl group having 6 to 50 carbon atoms include a phenyl group, a tolyl group, a naphthyl group, an acenaphthylenyl group, an anthryl group, a phenanthryl group, a phenarenyl group, a fluorenyl group, an a-indacenyl group, and an as-indacenyl group. Of those, an aryl group having 6 to 14 carbon atoms is preferred.

The aromatic diamine derivative represented by the general formula (I) is preferably such an aromatic diamine derivative as described below. When a represents 1, A represents a substituted or unsubstituted alkyl group having 1 to 50 carbon atoms, a substituted or unsubstituted cycloalkyl group having 3 to 50 carbon atoms, a substituted or unsubstituted aralkyl group having 7 to 50 carbon atoms, a substituted or unsubstituted alkyloxy group having 1 to 50 carbon atoms, or a substituted or unsubstituted aryl group having 6 to 50 carbon atoms. When a represents 2 to 5, at least one of the multiple A's represents a substituted or unsubstituted alkyl group having 1 to 50 carbon atoms, a substituted or unsubstituted cycloalkyl group having 3 to 50 carbon atoms, a substituted or unsubstituted aralkyl group having 7 to 50 carbon atoms, a substituted or unsubstituted alkyloxy group having 1 to 50 carbon atoms, or a substituted or unsubstituted aryl group having 6 to 50 carbon atoms.

In addition, the aromatic diamine derivative represented by the general formula (I) is preferably an aromatic diamine derivative in which only A and C each represent a substituted or unsubstituted silyl group.

Examples of the aromatic diamine derivative represented by the general formula (I) include the following compounds. It should be noted that —SiMe₃ represents a trimethylsilyl group.

[Chem 3]

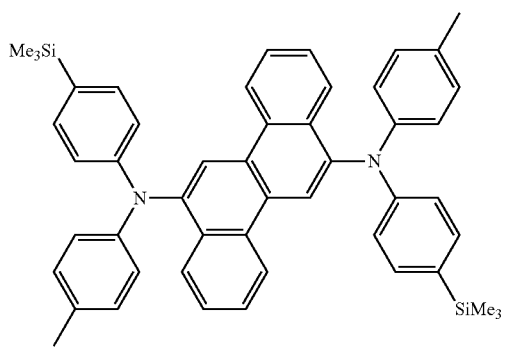

D-1

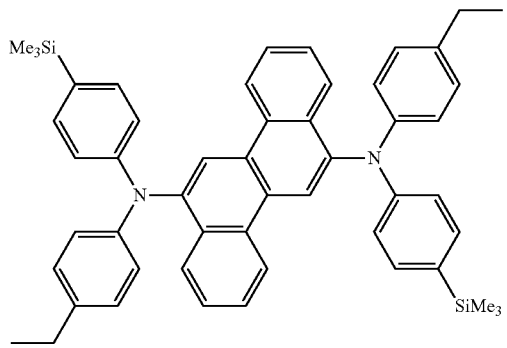

D-2

D-3

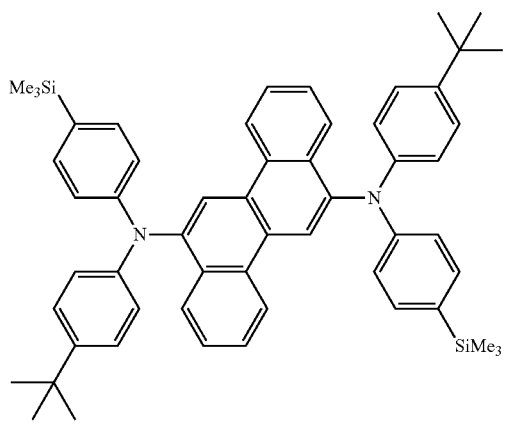

D-4

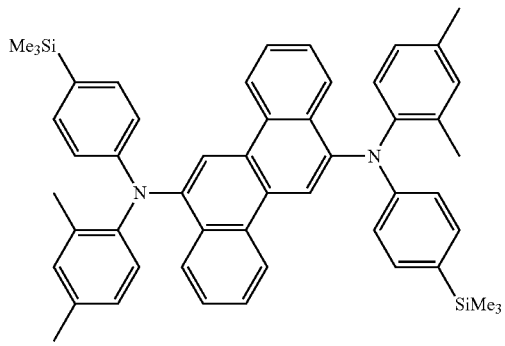

D-5

D-6
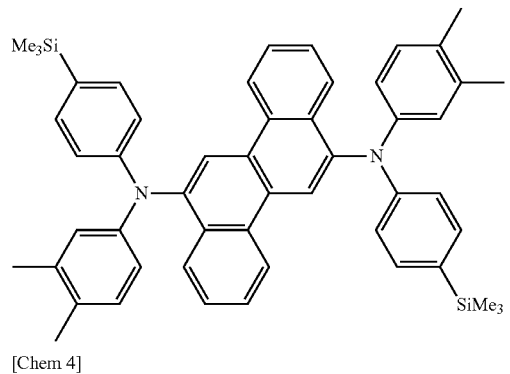
[Chem 4]
D-7
D-8
D-9
D-10
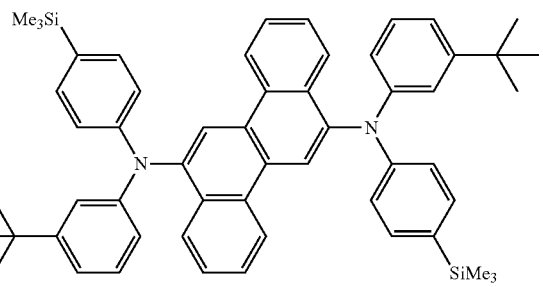
D-11
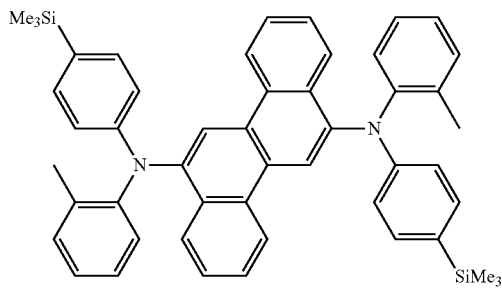
D-12
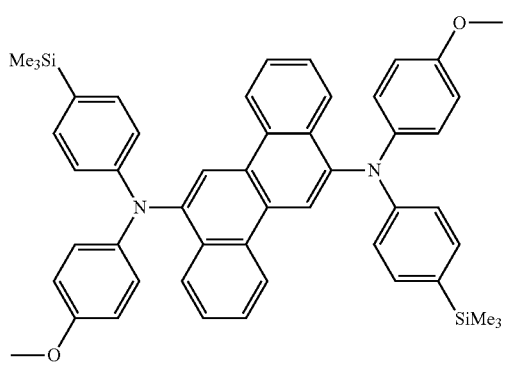
D-13
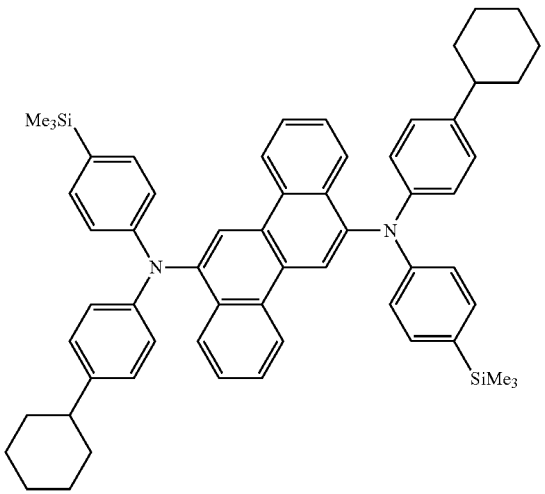

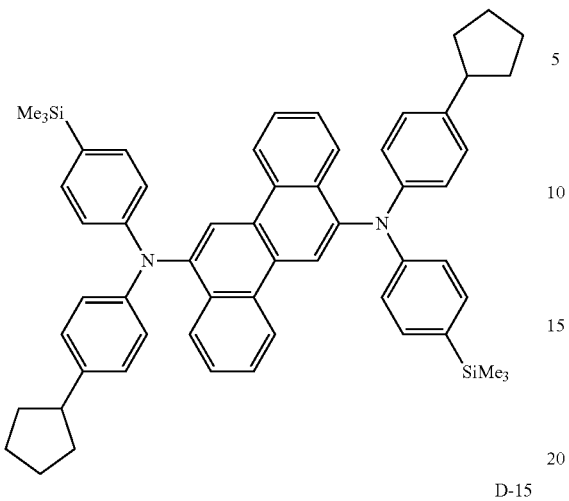

D-14

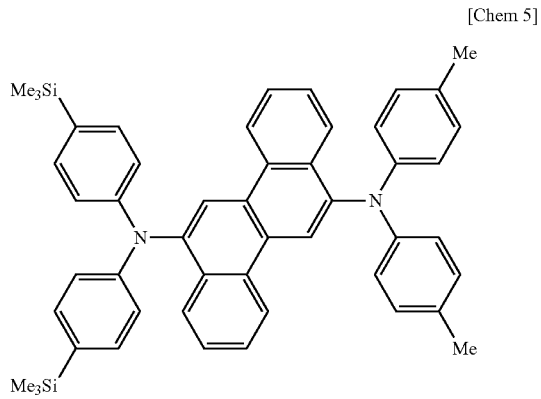 [SMILES: Cc1ccc(N(c2ccc(C)cc2)c2cc3c4ccccc4c(N(c4ccc([Si](C)(C)C)cc4)c4ccc([Si](C)(C)C)cc4)cc3c3ccccc23)cc1]

D-15

In the aromatic diamine derivative of the present invention, when B and C each represent a trimethylsilyl group, b and c each represent 1, and B and C each substitute at a para position, and when A and $R^{11}$ each represent a methyl group, a structure in which a and d simultaneously represent 1, and A and $R^{11}$ each substitute at a para position, i.e., the following compound is excluded.

[Chem 5]

In addition, in the aromatic diamine derivative, when A represents a trimethylsilyl group, a represents 1, and A substitutes at a para position, and when $R^{11}$ represents a methyl group, d represents 2, and the $R^{11}$'s each substitute at a meta position, a structure in which B represents a trimethylsilyl group, b represents 1, B substitutes at a para position, C represents a methyl group, c represents 2, and the C's each substitute at a meta position, i.e., the following compound is excluded.

[Chem 6]

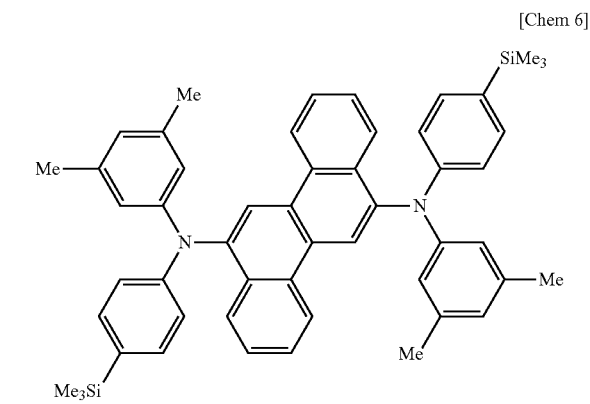 [SMILES: Cc1cc(C)cc(N(c2ccc([Si](C)(C)C)cc2)c2cc3c4ccccc4c(N(c4ccc([Si](C)(C)C)cc4)c4cc(C)cc(C)c4)cc3c3ccccc23)c1]

A method of producing the aromatic diamine derivative represented by the general formula (I) of the present invention is not particularly limited, and it is sufficient that the aromatic diamine derivative be produced by a known method. For example, the aromatic diamine derivative is produced by aminating 6,12-dibromochrysene obtained by the method described in Rev. Roum. Chim., 34, p. 1907 (1989) (M. D. Bancia et al.) with a diarylamine compound.

The aromatic diamine derivative of the present invention is suitably used as a material for an organic EL device, and is particularly preferably used as a light emitting material. The aromatic diamine derivative is suitably used as a blue light emitting material or a green light emitting material.

In addition, the aromatic diamine derivative of the present invention is more suitably used as a doping material for an organic EL device.

An organic EL device of the present invention is a device in which an organic thin film layer formed of one or more layers is formed between an anode and a cathode. When the device is of a one-layer type, a light emitting layer is provided between the anode and the cathode. The light emitting layer contains a light emitting material, and may contain a hole injecting material or an electron injecting material in addition to the light emitting material in order that a hole injected from the anode or an electron injected from the cathode may be transported to the light emitting material. The aromatic diamine derivative of the present invention can be used as a light emitting material or doping material in a light emitting layer because the aromatic diamine derivative has a high light emitting characteristic, an excellent hole injecting characteristic, an excellent hole transporting characteristic, an excellent electron injecting characteristic, and an excellent electron transporting characteristic.

In the organic EL device of the present invention, the light emitting layer preferably contains the aromatic diamine derivative of the present invention, and the content is preferably 0.1 to 20 mass %, more preferably 1 to 10 mass %, or still more preferably 3 to 7 mass % in ordinary cases. In addition, the light emitting layer can be formed only of the aromatic diamine derivative of the present invention because the aromatic diamine derivative brings together extremely high fluorescent quantum efficiency, a high hole transporting ability, and a high electron transporting ability, and enables the formation of a uniform thin film.

In addition, the organic EL device of the present invention is preferably an organic EL device having an organic thin film layer formed of two or more layers including at least a light emitting layer and interposed between a cathode and an anode in which an organic layer mainly formed of the aromatic diamine derivative of the present invention is placed between the anode and the light emitting layer. Examples of the organic layer include a hole injecting layer and a hole transporting layer.

Further, when the aromatic diamine derivative of the present invention is used as a doping material, a known compound can be used as a host material without any particular limitation. It is more preferred that an anthracene derivative represented by the following general formula (i) and/or a pyrene derivative represented by the following general formula (ii) be used.

[Chem 7]

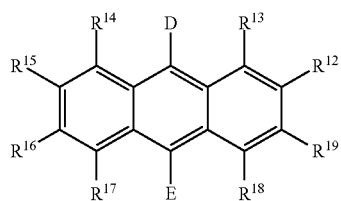

(i)

where $R^{12}$ to $R^{19}$ each independently represent a group selected from a hydrogen atom, a substituted or unsubstituted aryl group having 6 to 50 carbon atoms, a substituted or unsubstituted heteroaryl group having 4 to 50 carbon atoms, a substituted or unsubstituted alkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aralkyl group whose aryl portion has 6 to 50 carbon atoms and whose alkyl portion has 1 to 50 carbon atoms, a substituted or unsubstituted aryloxy group having 5 to 50 carbon atoms, a substituted or unsubstituted arylthio group having 5 to 50 carbon atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group, and D and E each independently represent a group derived from a substituted or unsubstituted aromatic ring having 6 to 20 carbon atoms.

Examples of the substituted or unsubstituted aryl group having 6 to 50 carbon atoms represented by any one of $R^{12}$ to $R^{19}$ in the general formula (i) include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4''-t-butyl-p-terphenyl-4-yl group.

Examples of the substituted or unsubstituted heteroaryl group having 4 to 50 carbon atoms represented by any one of $R^{12}$ to $R^{19}$ in the general formula (i) include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, and a 4-t-butyl-3-indolyl group.

Examples of the substituted or unsubstituted alkyl group having 1 to 50 carbon atoms represented by any one of $R^{12}$ to $R^{19}$ in the general formula (i) include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, aniodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, and a 1,2,3-trinitropropyl group.

Examples of the substituted or unsubstituted cycloalkyl group having 3 to 50 carbon atoms represented by any one of $R^{12}$ to $R^{19}$ in the general formula (i) include a cyclopropyl group, a cyclobutyl group, a cyclopentyl group, a cyclohexyl group, a 4-methylcyclohexyl group, a 1-adamantyl group, a 2-adamantyl group, a 1-norbornyl group, and a 2-norbornyl group.

An alkyl group site of the substituted or unsubstituted alkoxyl group having 1 to 50 carbon atoms represented by any one of $R^{12}$ to $R^{19}$ in the general formula (i) is selected from the substituted or unsubstituted alkyl groups each having 1 to 50 carbon atoms represented by $R^{12}$ to $R^{19}$.

Examples of the substituted or unsubstituted aralkyl group (whose aryl portion has 6 to 50 carbon atoms and whose alkyl portion has 1 to 50 carbon atoms) as the substituents represented by any one of $R^{12}$ to $R^{19}$ in the general formula (i) include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group.

Aryl group sites of the substituted or unsubstituted aryloxy group having 6 to 50 carbon atoms and the substituted or unsubstituted arylthio group having 6 to 50 carbon atoms each represented by any one of $R^{12}$ to $R^{19}$ in the general formula (i) are each selected from the substituted or unsubstituted aryl groups each having 6 to 50 carbon atoms represented by $R^{12}$ to $R^{19}$.

Examples of the substituted or unsubstituted alkoxycarbonyl group having 1 to 50 carbon atoms represented by anyone of $R^{12}$ to $R^{19}$ in the general formula (i) include a methoxycarbonyl group, an ethoxycarbonyl group, various propoxycarbonyl groups, and various butoxycarbonyl groups. Of those, an alkoxycarbonyl group having 1 to 20 carbon atoms is preferred.

Examples of the substituted silyl group represented by any one of $R^{12}$ to $R^{19}$ in the general formula (i) include a trimethylsilyl group, a triethylsilyl group, a t-butyldimethylsilyl group, a vinyldimethylsilyl group, a propyldimethylsilyl group, and a triphenylsilyl group.

Examples of the halogen atom represented by any one of $R^{12}$ to $R^{19}$ in the general formula (i) include a fluorine atom, a chlorine atom, a bromine atom, and an iodine atom.

The substituent of an aromatic ring represented by any one of $R^{12}$ to $R^{19}$ may be further substituted by a halogen atom, a hydroxyl group, a nitro group, a cyano group, an alkyl group having 1 to 10 carbon atoms, an aryl group having 1 to 30 carbon atoms, a cycloalkyl group having 3 to 20 carbon atoms, an alkoxyl group having 1 to 10 carbon atoms, an aromatic heterocyclic group having 5 to 30 carbon atoms, an aralkyl group having 7 to 30 carbon atoms, an aryloxy group having 6 to 30 carbon atoms, an arylthio group having 6 to 30 carbon atoms, an alkoxycarbonyl group having 2 to 10 carbon atoms, a carboxyl group, or the like.

D and E each independently represent a group derived from a substituted or unsubstituted aromatic ring having 6 to 20 carbon atoms. The aromatic ring may be substituted with one or more substituents. Any such substituent for the aromatic ring is selected from a substituted or unsubstituted aryl group having 6 to 50 carbon atoms, a substituted or unsubstituted alkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aralkyl group (whose aryl portion has 6 to 50 carbon atoms and whose alkyl portion has 1 to 5 carbon atoms), a substituted or unsubstituted aryloxy group having 6 to 50 carbon atoms, a substituted or unsubstituted arylthio group having 6 to 50 carbon atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group, and these groups are selected from groups described as specific examples of $R^{12}$ to $R^{19}$. When the aromatic ring is substituted with two or more substituents, the substituents may be identical to or different from each other, and substituents adjacent to each other may be bonded to each other to form a saturated or unsaturated cyclic structure.

In addition, at least one of D and E preferably represents a substituent having a substituted or unsubstituted fused ring group having 10 to 30 carbon atoms, or more preferably represents a substituent having a substituted or unsubstituted naphthyl group.

It should be noted that D and E are preferably different from each other.

Examples of the group derived from a substituted or unsubstituted aromatic ring having 6 to 20 carbon atoms represented by any one of D and E include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, and a 4''-t-butyl-p-terphenyl-4-yl group. A group derived from a substituted or unsubstituted aromatic ring having 10 to 14 ring carbon atoms is preferred. In particular, a 1-naphthyl group, a 2-naphthyl group, and a 9-phenanthryl group are preferred.

The substituents of the aromatic ring represented by D and E may each be further substituted with, for example, a halogen atom, a hydroxyl group, a nitro group, a cyano group, an alkyl group having 1 to 10 carbon atoms, an aryl group having 1 to 30 carbon atoms, a cycloalkyl group having 3 to 20 carbon atoms, an alkoxyl group having 1 to 10 carbon atoms, an aromatic heterocyclic group having 5 to 30 carbon atoms, an aralkyl group having 7 to 30 carbon atoms, an aryloxy group having 6 to 30 carbon atoms, an arylthio group having 6 to 30 carbon atoms, an alkoxycarbonyl group having 2 to 10 carbon atoms, or a carboxyl group.

[Chem 8]

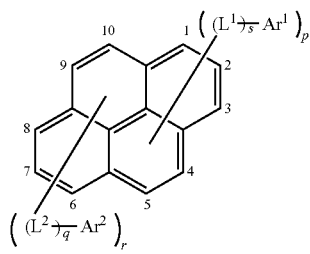

(ii)

In the formula:
$Ar^1$ and $Ar^2$ each independently represent a substituted or unsubstituted aryl group having 6 to 50 carbon atoms;
$L^1$ and $L^2$ each independently represent a substituted or unsubstituted phenylene group, a substituted or unsubstituted naphthalenylene group, a substituted or unsubstituted fluorenylene group, or a substituted or unsubstituted dibenzosilolylene group;

s represents an integer of 0 to 2, p represents an integer of 1 to 4, q represents an integer of 0 to 2, and r represents an integer of 0 to 4; and
$L^1$ or $Ar^2$ is bonded to any one of 1- to 5-positions of pyrene and $L^2$ or $Ar^2$ is bonded to any one of 6- to 10-positions of pyrene,
provided that, when p+r is an even number, $Ar^1$, $Ar^2$, $L^1$, and $L^2$ satisfy the following condition (1) or (2):
(1) $Ar^1 \neq Ar^2$ and/or $L^1 = L^2$ where ≠ means that groups on both of its sides are different from each other in structure; or
(2) when $Ar^1 = Ar^2$ and $L^1 = L^2$,
  (2-1) s≠q and/or p≠r, or
  (2-2) if s=q and p=r,
    (2-2-1) $L^1$ and $L^2$ are, or pyrene is, bonded to different bonding positions on $Ar^1$ and $Ar^2$, or (2-2-2) in a case where $L^1$ and $L^2$ are, or pyrene is, bonded to the same bonding positions on $Ar^1$ and $Ar^1$, substitution positions of $L^1$ and $L^2$ or $Ar^1$ and $Ar^2$ on pyrene exclude 1- and 6-positions or 2- and 7-positions.

Examples of the aryl group having 6 to 50 carbon atoms represented by each of $Ar^1$ and $Ar^2$ include a phenyl group, a 2-methylphenyl group, a 3-methylphenyl group, a 4-methylphenyl group, a 4-ethylphenyl group, a biphenyl group, a 4-methylbiphenyl group, a 4-ethylbiphenyl group, a 4-cyclohexylbiphenyl group, a 3,5-dichlorophenyl group, a naphthyl group, a 5-methylnaphthyl group, an acenaphthylenyl group, an anthryl group, a phenanthryl group, a phenarenyl group, a fluorenyl group, an a-indacenyl group, and an as-indacenyl group. Of those, an aryl group having 6 to 30 carbon atoms is particularly preferred.

A substituent which the phenylene group, naphthalenylene group, fluorenylene group, or dibenzosilolylene group represented by each of $L^1$ and $L^2$ may have is, for example, an alkyl group having 1 to 50 carbon atoms, a cycloalkyl group having 3 to 50 carbon atoms, an aralkyl group having 7 to 50 carbon atoms, an alkoxyl group having 1 to 50 carbon atoms, an aryl group having 6 to 50 carbon atoms, an aryloxy group having 6 to 50 carbon atoms, an arylthio group having 6 to 50 carbon atoms, an alkoxycarbonyl group having 1 to 50 carbon atoms, an amino group, a halogen atom, a nitro group, a hydroxyl group, a carboxyl group, or a cyano group.

Examples of the alkyl group having 1 to 50 carbon atoms include a methyl group, an ethyl group, an n-propyl group, an isopropyl group, an n-butyl group, an isobutyl group, an s-butyl group, a t-butyl group, and various pentyl groups. Of those, an alkyl group having 1 to 10 carbon atoms is preferred.

Examples of the cycloalkyl group having 3 to 50 carbon atoms include a cyclopropyl group, a cyclopentyl group, a cyclohexyl group, a 4-methylcyclohexyl group, and a cyclooctyl group. Of those, a cyclohexyl group having 5 to 8 carbon atoms is preferred.

Examples of the aralkyl group having 7 to 50 carbon atoms include a benzyl group, an α,α-phenylmethylbenzyl group, an α,α-dimethylbenzyl group, an α-phenoxybenzyl group, an α,α-methylphenylbenzyl group, an α,α-ditrifluoromethylbenzyl group, a triphenylmethyl group, an α-benzyloxybenzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, a 1-pyrrolylmethyl group, a 2-(1-pyrrolyl)ethyl group, a p-methylbenzyl group, an m-methylbenzyl group, an o-methylbenzyl group, a p-chlorobenzyl group, an m-chlorobenzyl group, an o-chlorobenzyl group, a p-bromobenzyl group, an m-bromobenzyl group, an o-bromobenzyl group, a p-iodobenzyl group, an m-iodobenzyl group, an o-iodobenzyl group, a p-hydroxybenzyl group, an m-hydroxybenzyl group, an o-hydroxybenzyl group, a p-aminobenzyl group, an m-aminobenzyl group, an o-aminobenzyl group, a p-nitrobenzyl group, an m-nitrobenzyl group, an o-nitrobenzyl group, a p-cyanobenzyl group, an m-cyanobenzyl group, an o-cyanobenzyl group, a 1-hydroxy-2-phenylisopropyl group, and a 1-chloro-2-phenylisopropyl group. Of those, an aralkyl group having 7 to 20 carbon atoms is preferred.

Examples of the alkoxyl group having 1 to 50 carbon atoms include a methoxy group, an ethoxy group, an n-propoxy group, an isopropoxy group, an n-butoxy group, an isobutoxy group, an s-butoxy group, and a t-butoxy group. Of those, an alkoxyl group having 1 to 10 carbon atoms is preferred.

Examples of the aryl group having 6 to 50 carbon atoms include a phenyl group, a naphthyl group, an acenaphthylenyl group, an anthryl group, a phenanthryl group, a phenarenyl group, a fluorenyl group, an a-indacenyl group, and an as-indacenyl group. Of those, an aryl group having 6 to 14 carbon atoms is preferred.

Examples of the aryloxy group having 6 to 50 carbon atoms include a phenoxy group and a naphthyloxy group. Of those, an aryloxy group having 6 to 20 carbon atoms is preferred.

Examples of the arylthio group having 6 to 50 carbon atoms include a phenylthio group and a naphthylthio group. Of those, an arylthio group having 6 to 20 carbon atoms is preferred.

Examples of the alkoxycarbonyl group having 1 to 50 carbon atoms include a methoxycarbonyl group, an ethoxycarbonyl group, various propoxycarbonyl groups, and various butoxycarbonyl groups. Of those, an alkoxycarbonyl group having 1 to 20 carbon atoms is preferred.

Examples of the amino group include amino groups each substituted with an alkyl group having 1 to 50 carbon atoms or with an aryl group having 6 to 50 carbon atoms such as a dimethylamino group, a diethylamino group, a diphenylamino group, and a dinaphthylamino group.

Examples of the halogen atom include a fluorine atom, a chlorine atom, a bromine atom, and an iodine atom.

Specific examples of the anthracene derivative represented by the general formula (i) to be used in the organic EL device of the present invention include various known anthracene derivatives such as an anthracene derivative having two anthracene skeletons in its molecule described in paragraphs [0043] to [0063] of JP 2004-356033 A and a compound having one anthracene skeleton described in p. 27 and 28 of WO 2005/061656 A1. Representative specific examples are shown below, but the derivative is not particularly limited thereto.

[Chem 9]

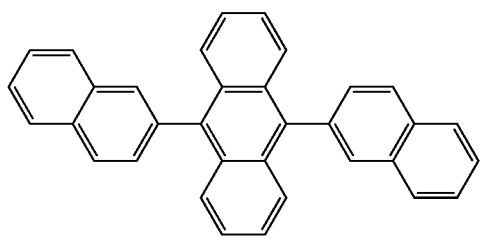
2a-1

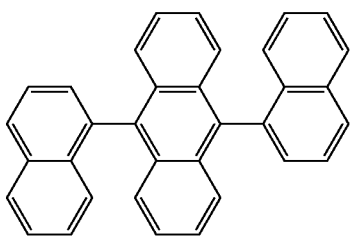
2a-2

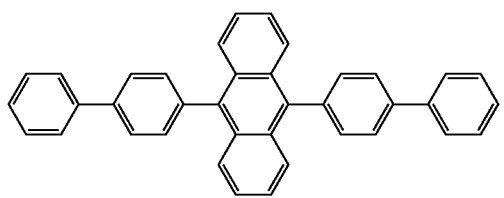
2a-3

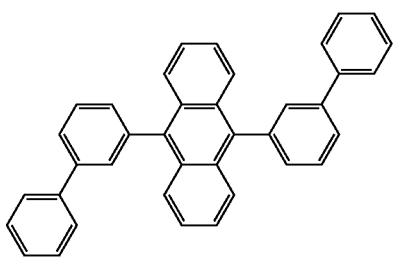
2a-4

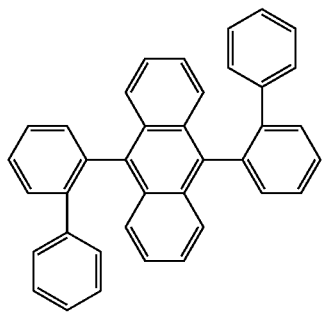
2a-5

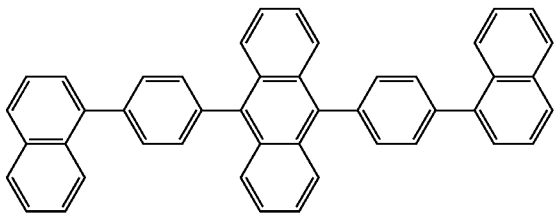
2a-6

-continued
2a-7
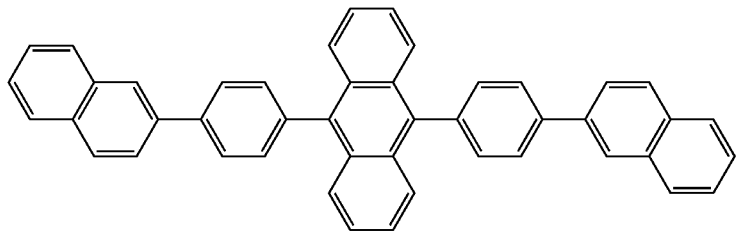
2a-8
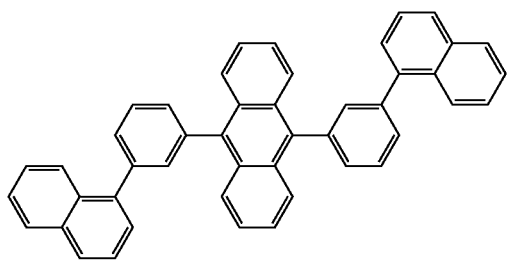
2a-9
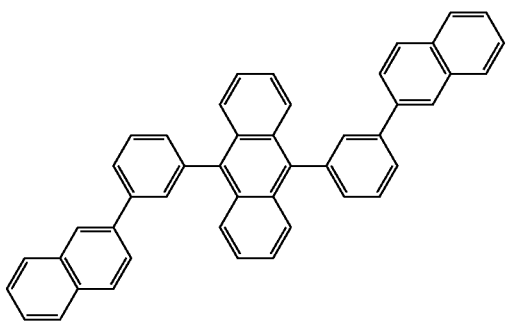
2a-10
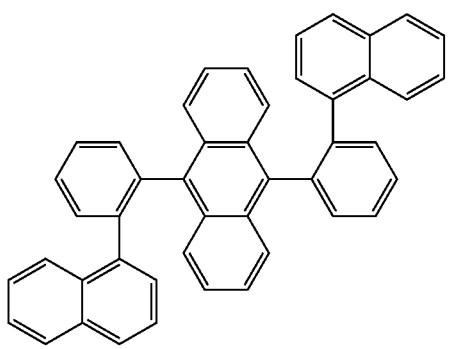
2a-11
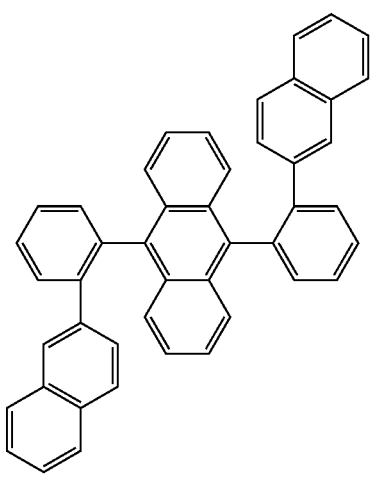
2a-12
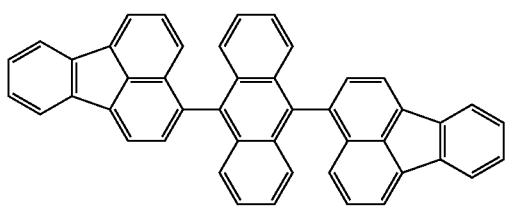
2a-13
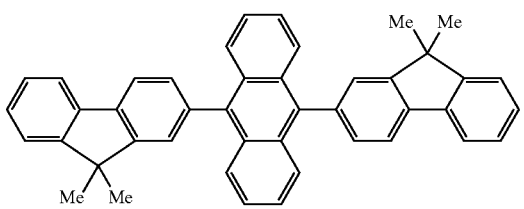
2a-14
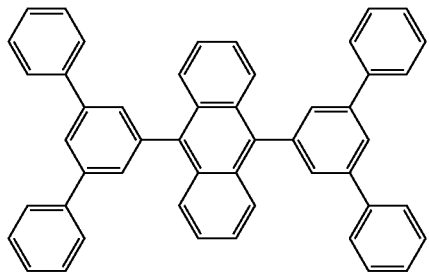
2a-15
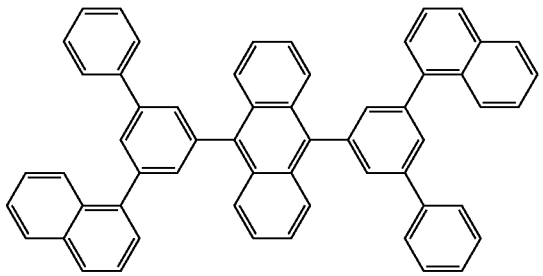

2a-16
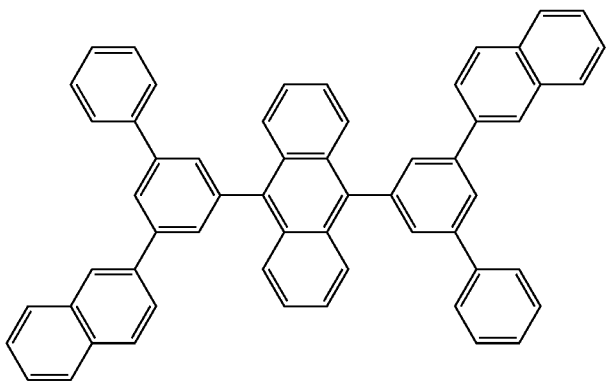
[Chem 10]
2a-17
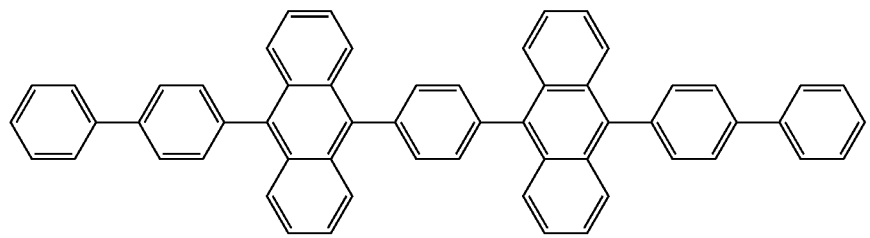
2a-18
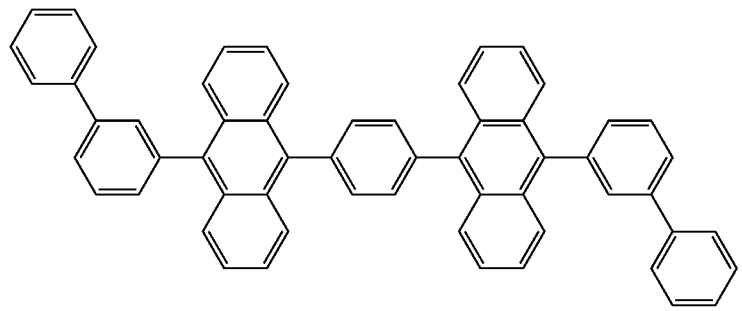
2a-19
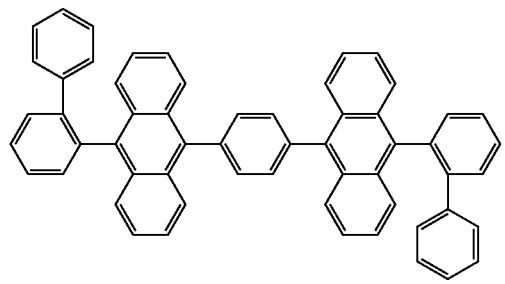
2a-20
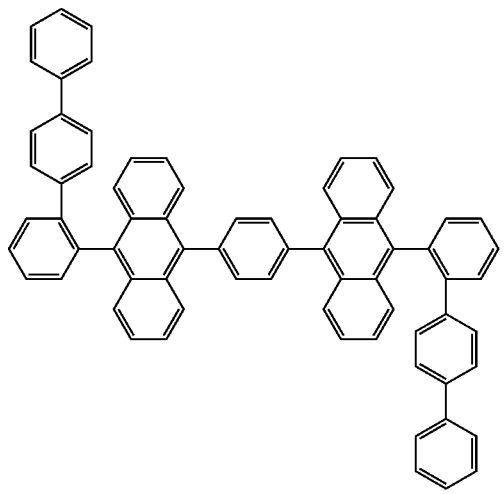

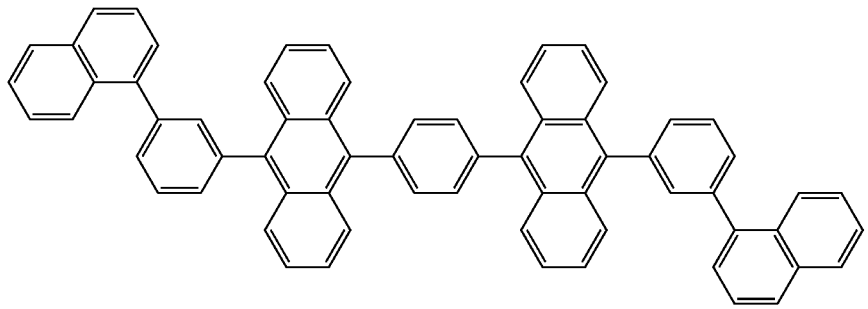

-continued
2a-27
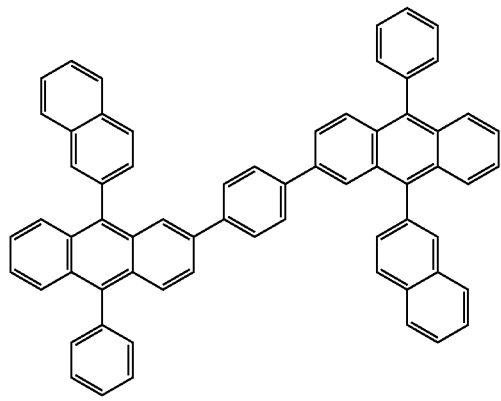
2a-28
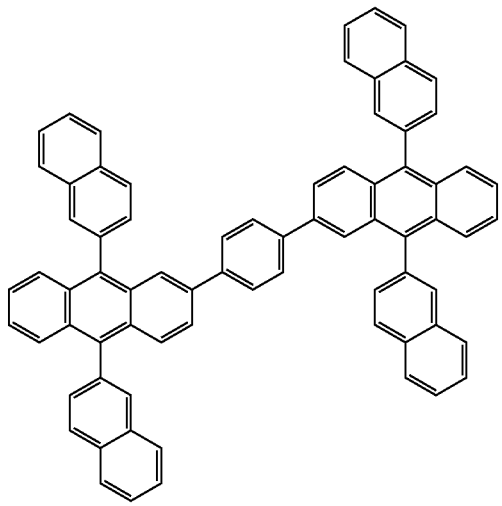
[Chem 11]
2a-29
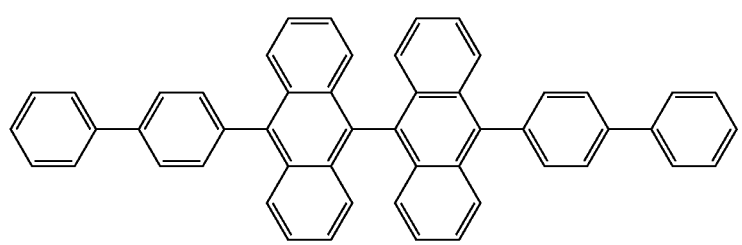
2a-30
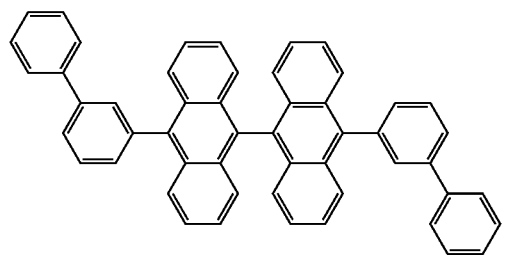
2a-31
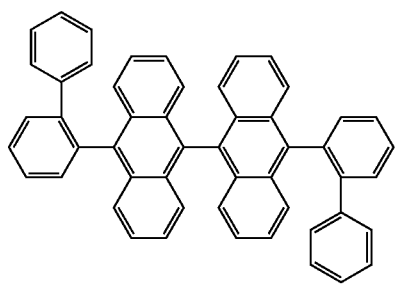
2a-32
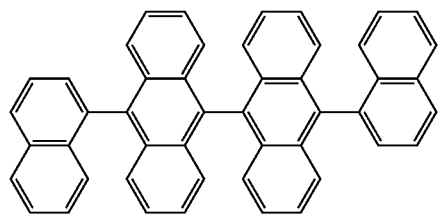
2a-33
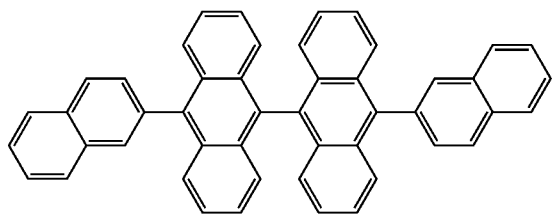

-continued
2a-34
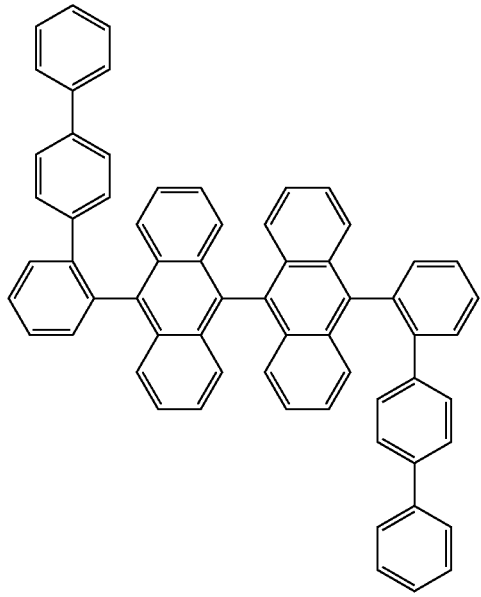
2a-35
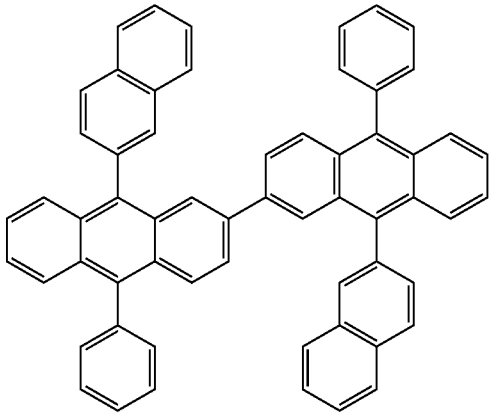
2a-36
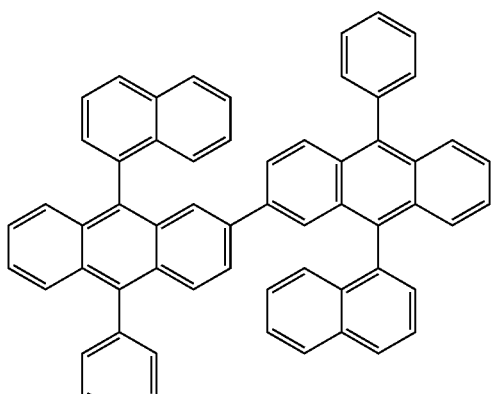
2a-37
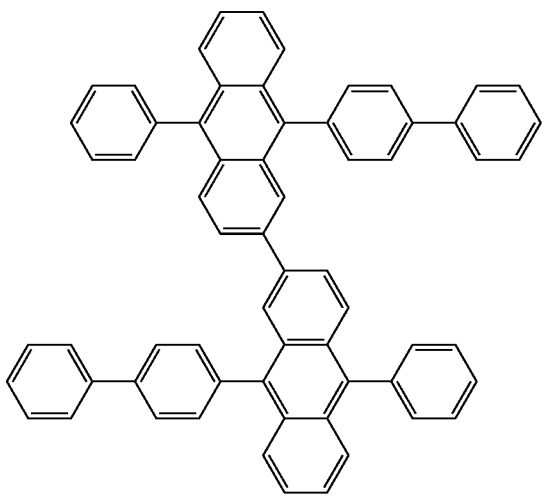
2a-38
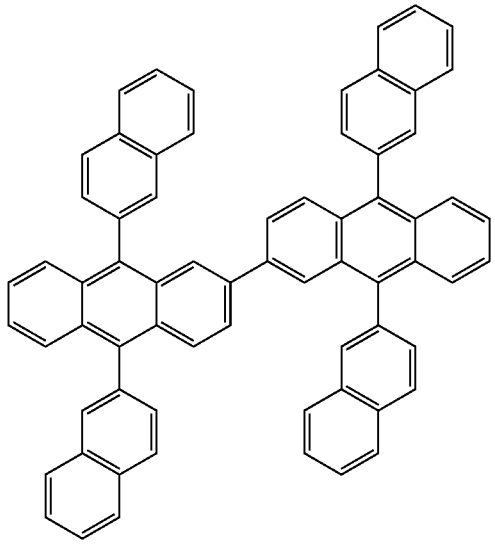
2a-39
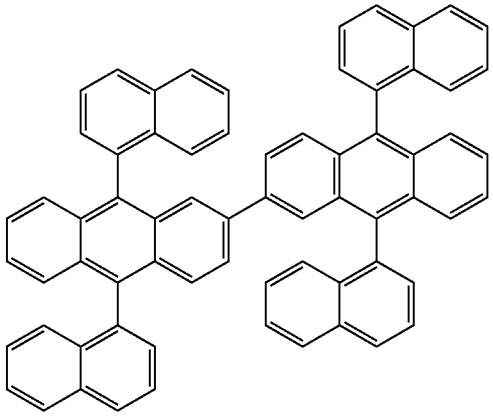

-continued
2a-40
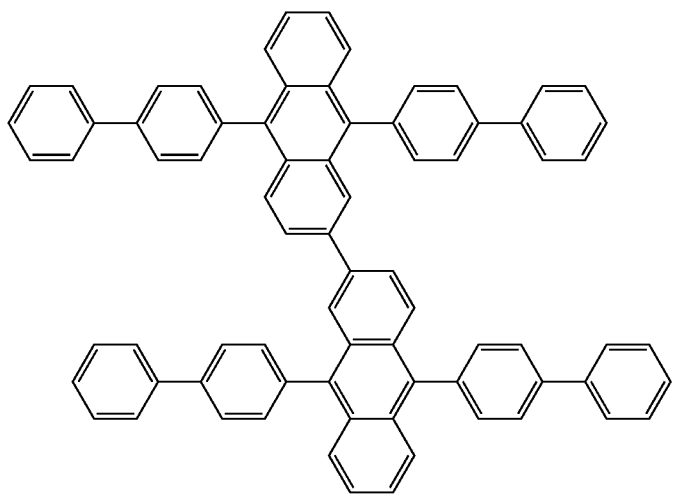
[Chem 12]
2a-41
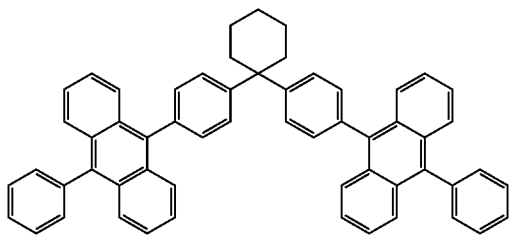
2a-42
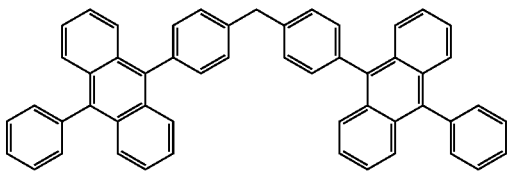
2a-43
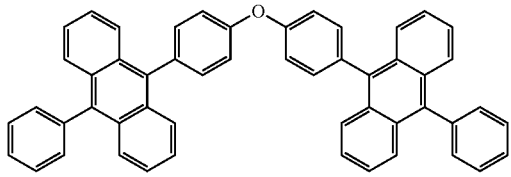
2a-44
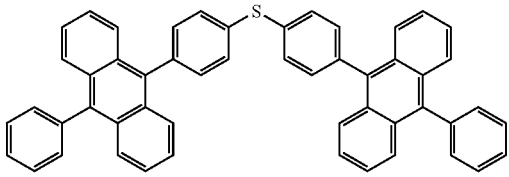
2a-45
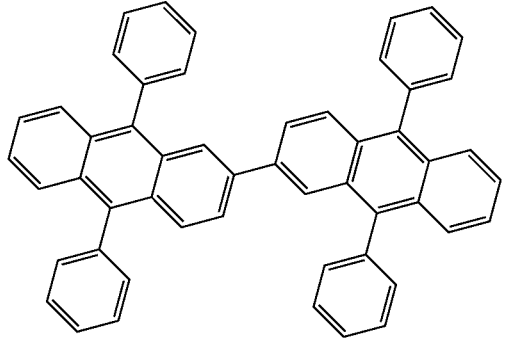

2a-46
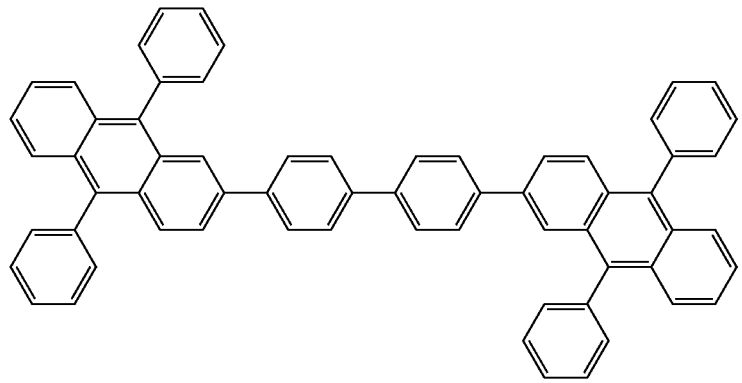
2a-47
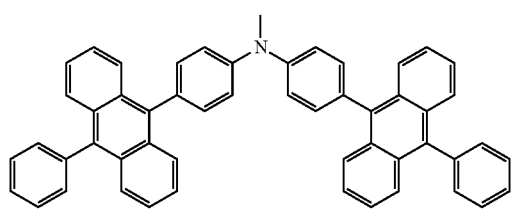
2a-48
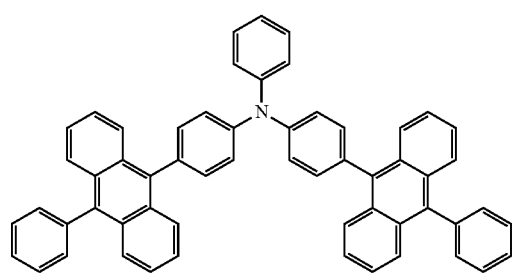
2a-49
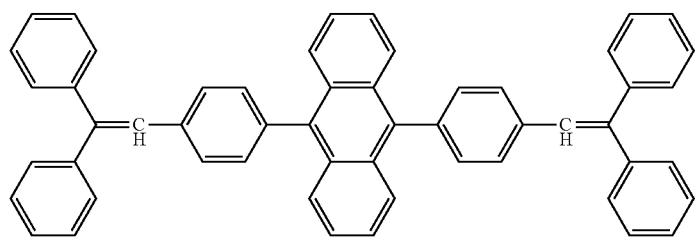
2a-50
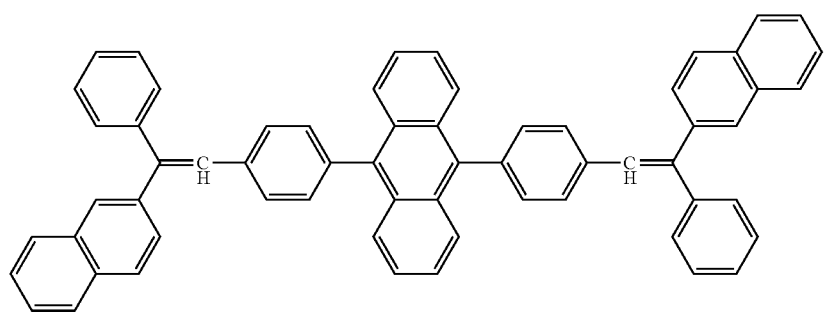

2a-51
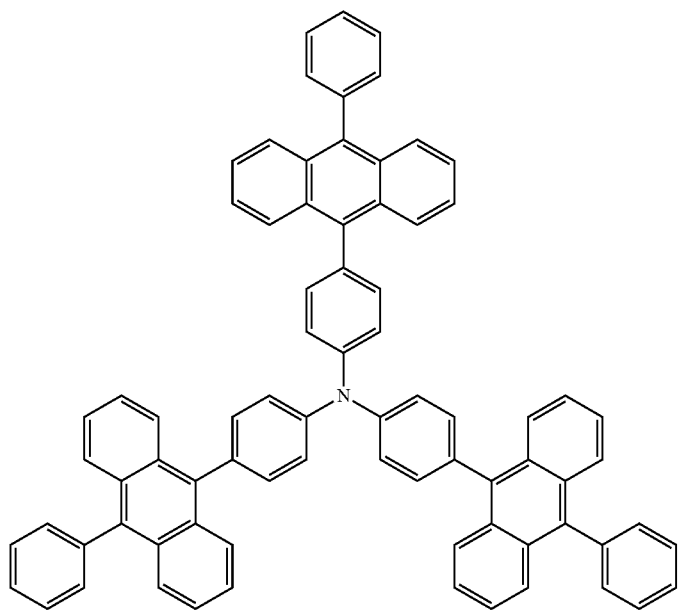
[Chem 13]
2a'-52    2a'-53
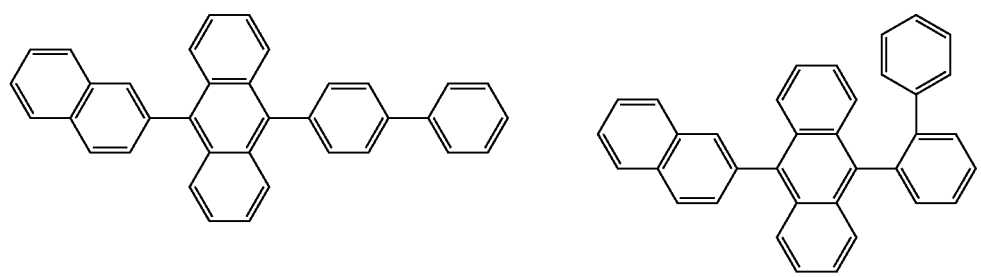
2a'-54    2a'-55
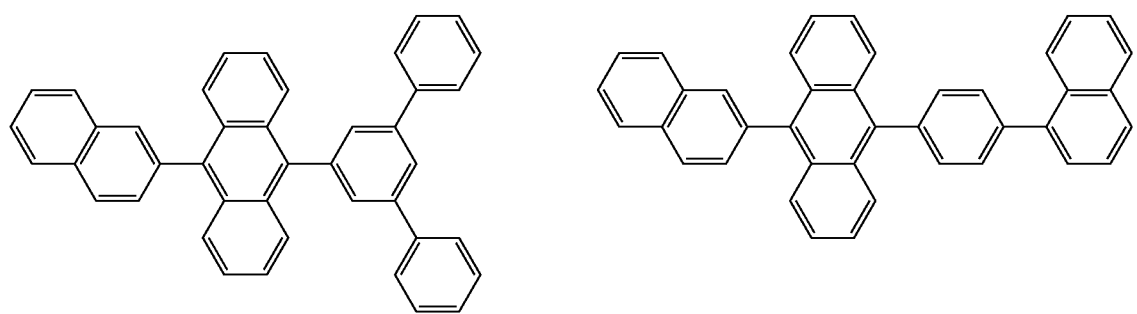

-continued
2a'-56
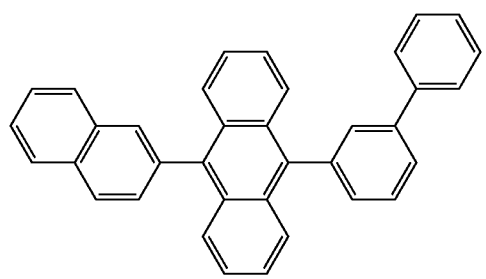
2a'-57
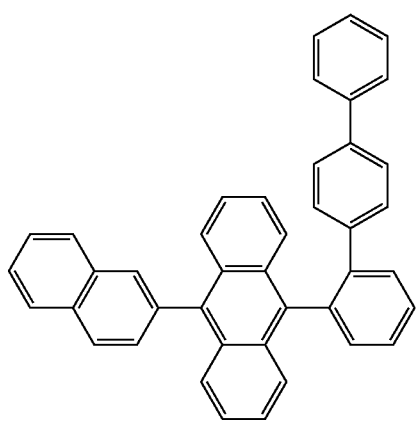
2a'-58
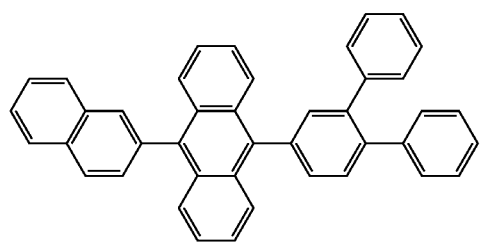
2a'-59
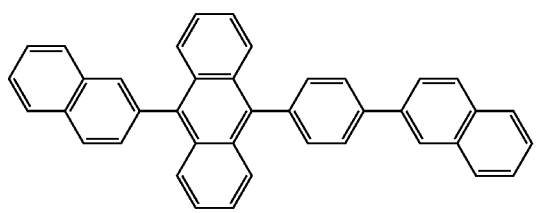
2a'-60
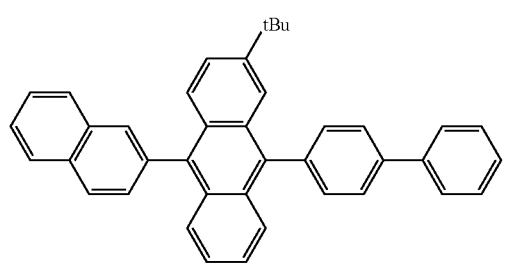
2a'-61
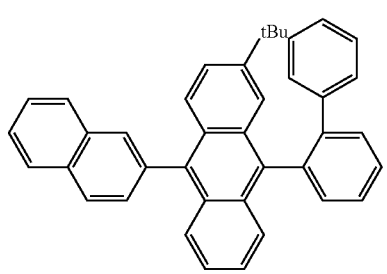
2a'-62
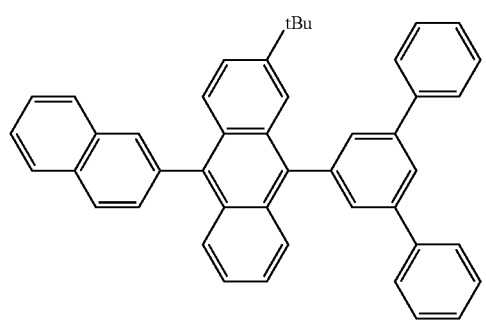
2a'-63
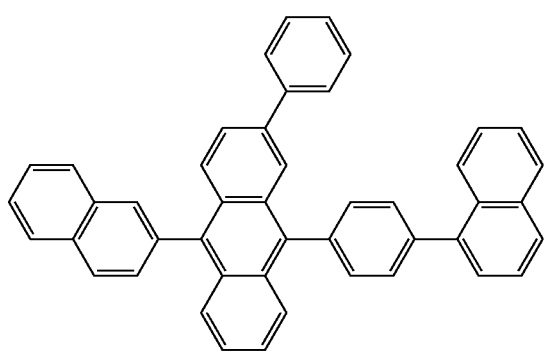

-continued
2a'-64
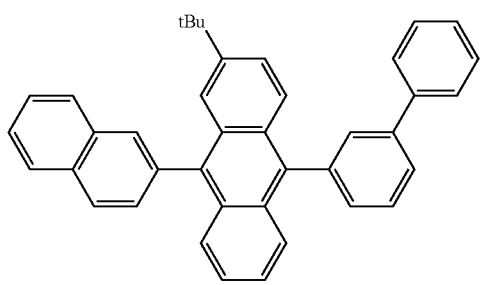
2a'-65
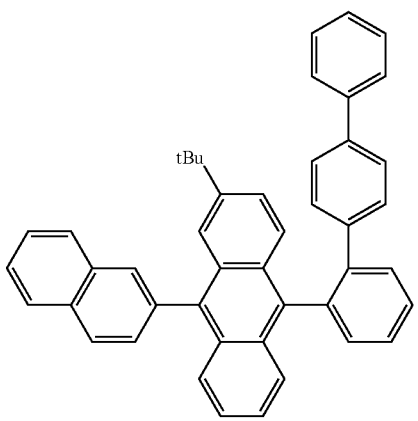
2a'-66
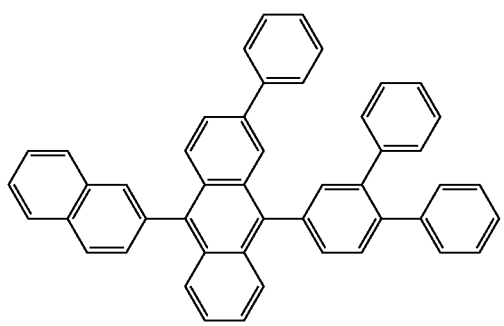
2a'-67
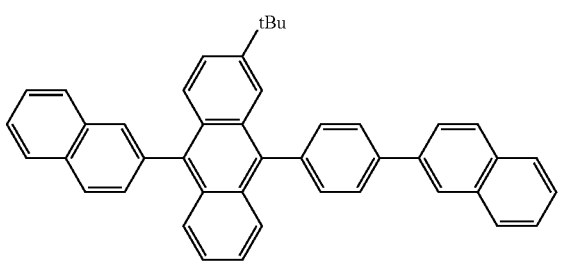
[Chem 14]
2a'-68
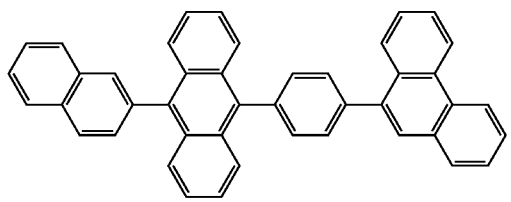
2a'-69
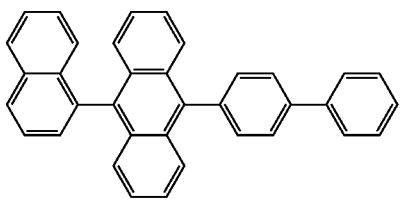
2a'-70
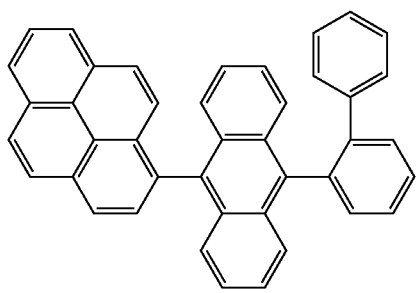
2a'-71
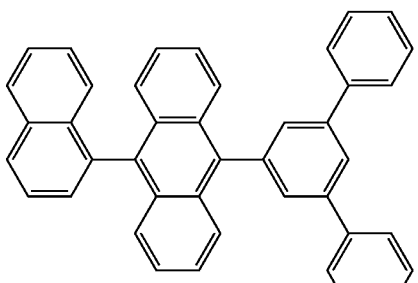
2a'-72
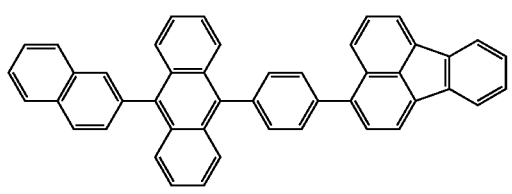
2a'-73
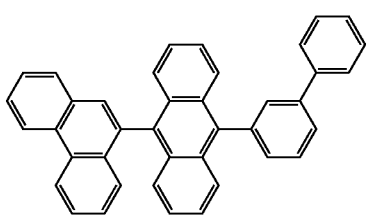

2a′-74
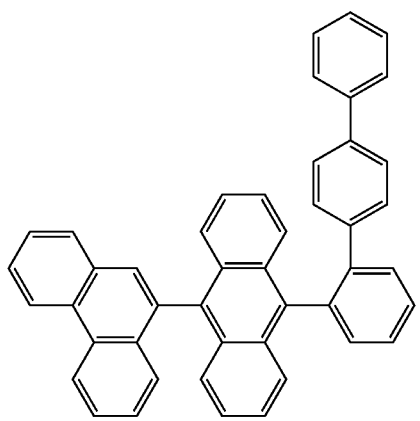
2a′-75
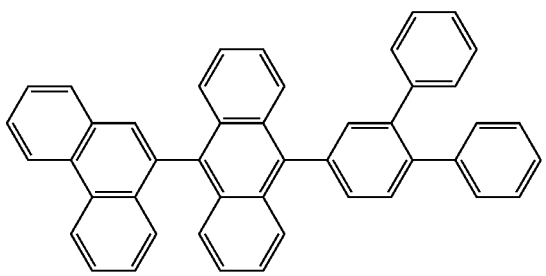
2a′-76
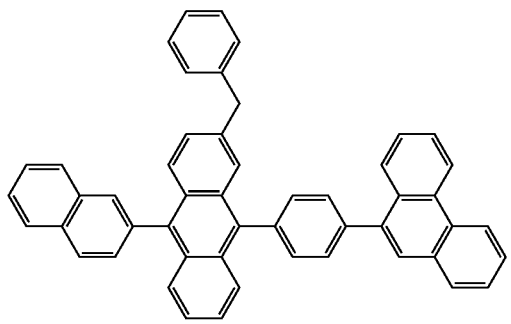
2a′-77
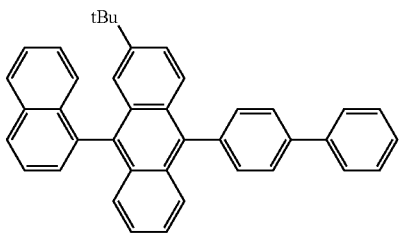
2a′-78
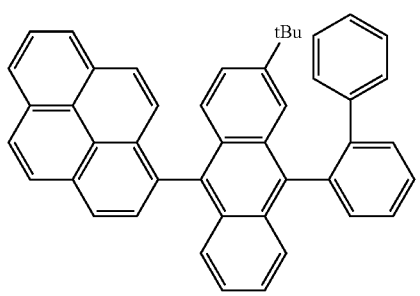
2a′-79
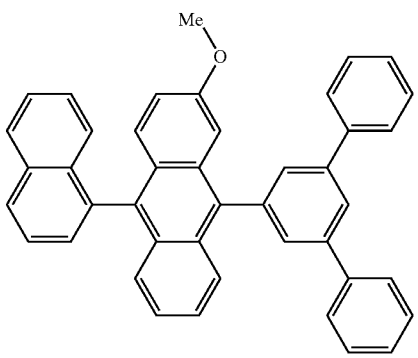
2a′-80
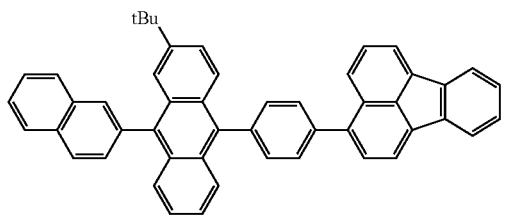
2a′-81
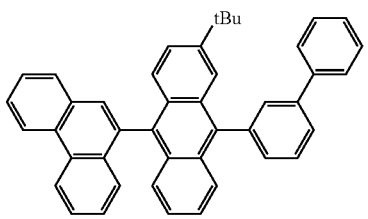

-continued
2a'-82
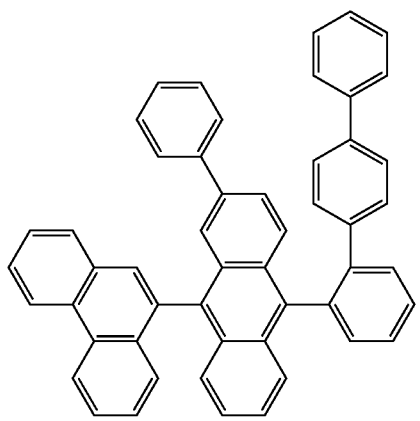
2a'-83
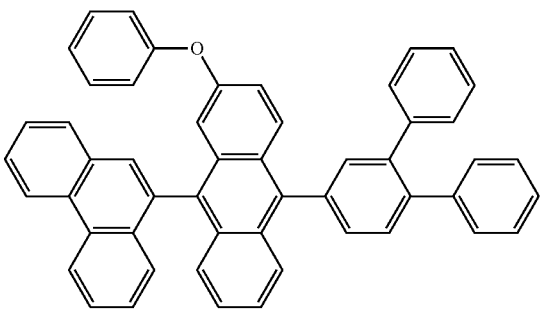
[Chem 15]
2a'-84
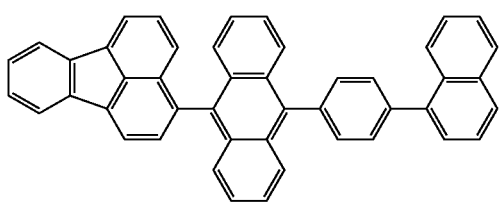
2a'-85
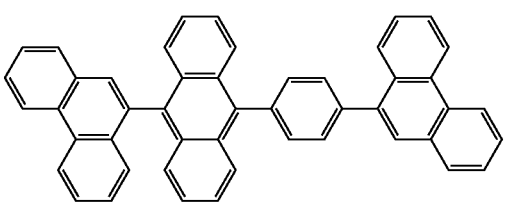
2a'-86
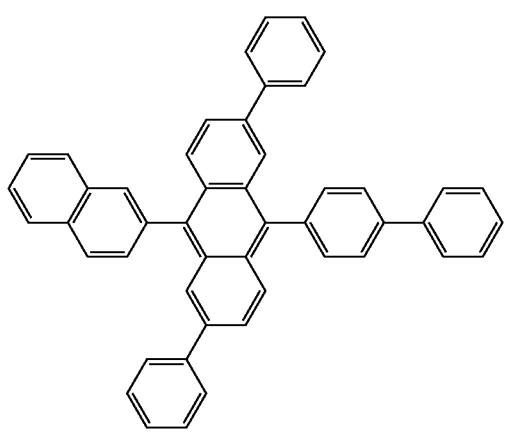
2a'-87
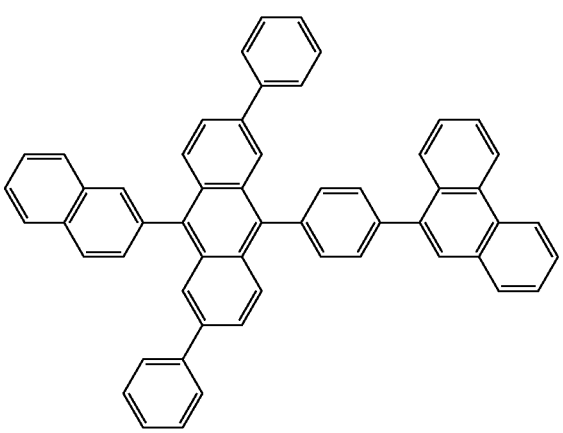
2a'-88
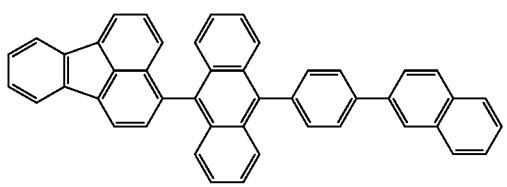
2a'-89
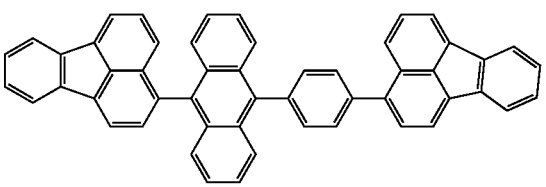

-continued
2a′-90
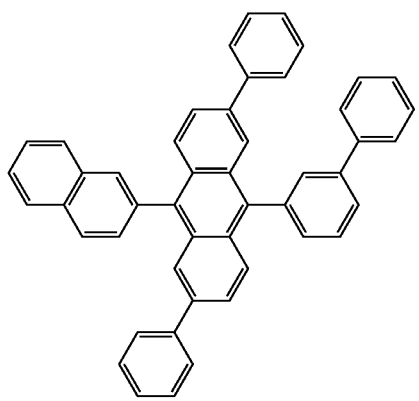
2a′-91
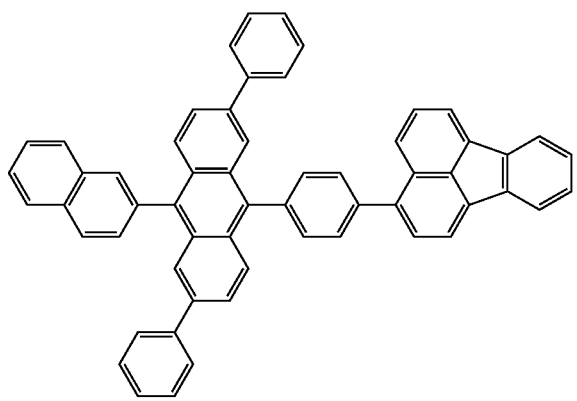
2a′-92
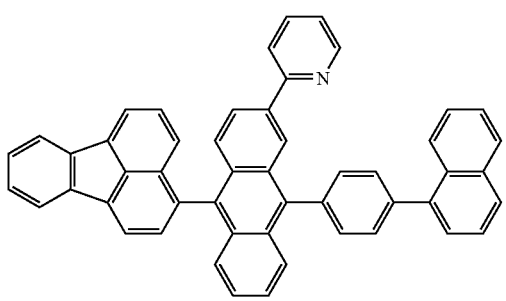
2a′-93
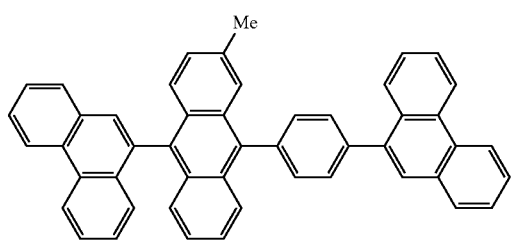
2a′-94
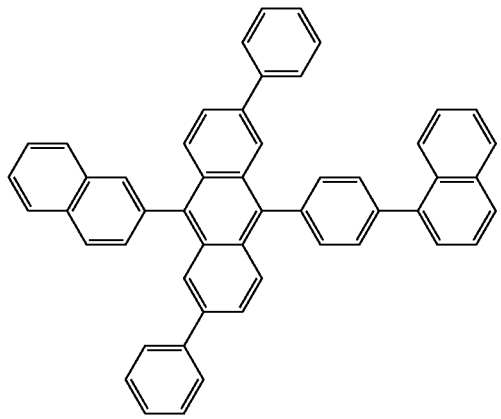
2a′-95
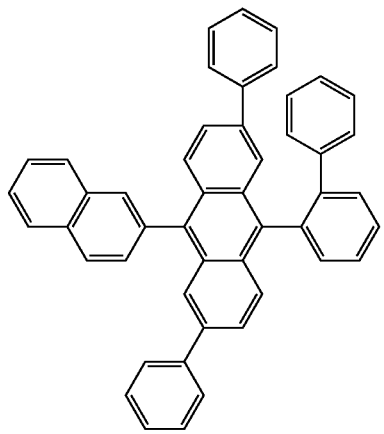
2a′-96
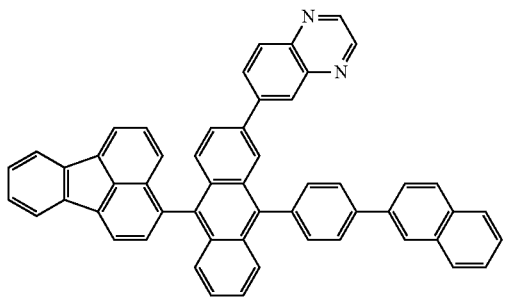
2a′-97
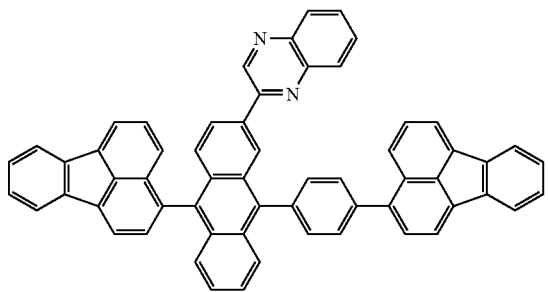

-continued
2a′-98
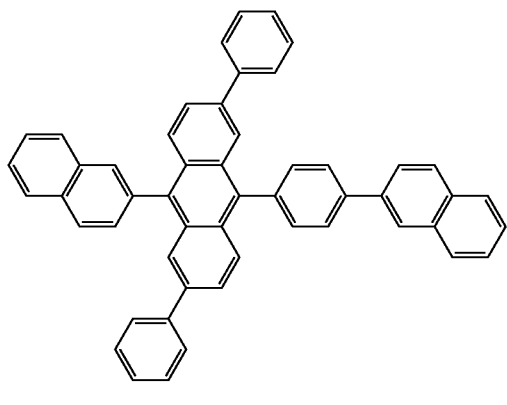
2a′-99
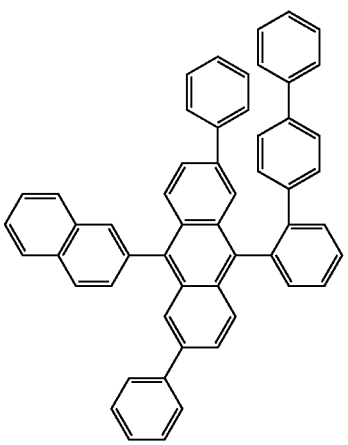
[Chem 16]
2a′-100
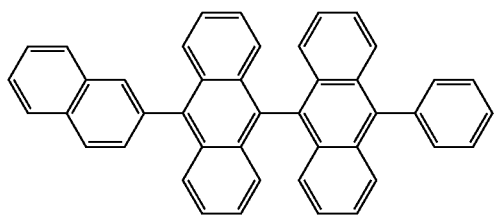
2a′-101
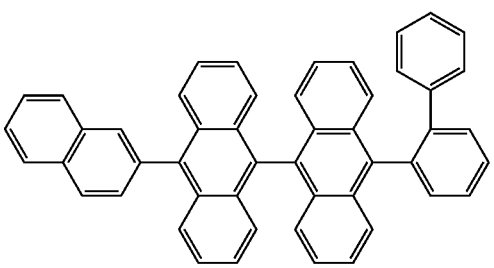
2a′-102
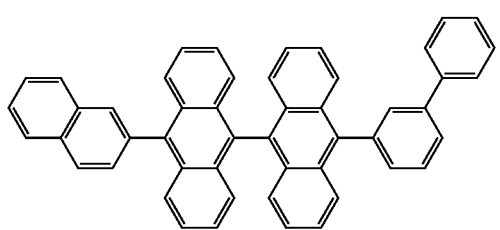
2a′-103
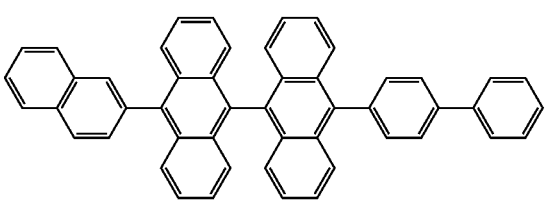
2a′-104
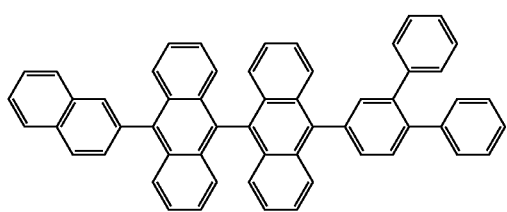
2a′-105
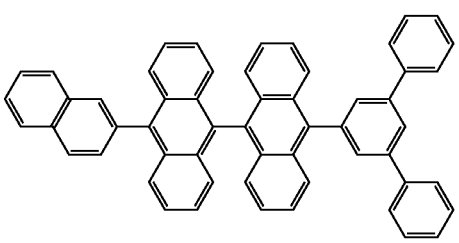
2a′-106
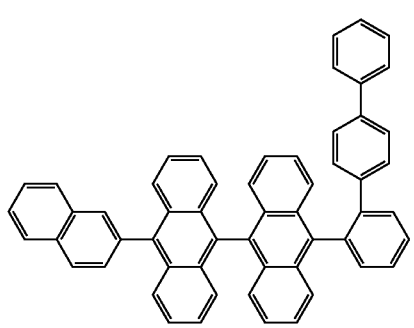
2a′-107
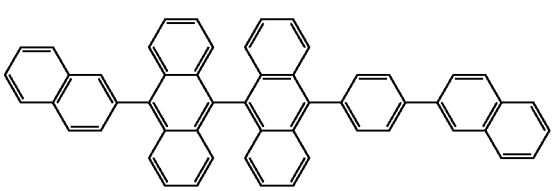

2a′-108
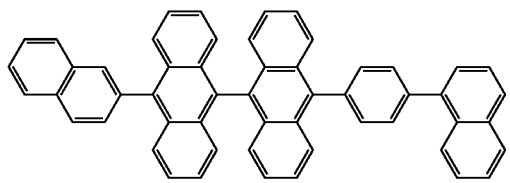
2a′-109
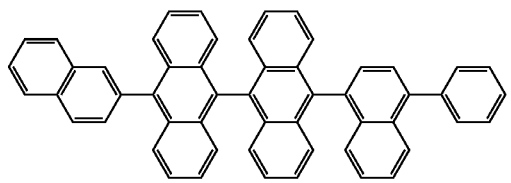
2a′-110
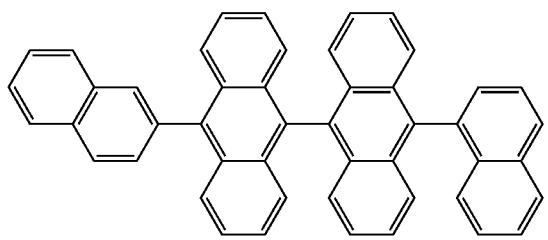
2a′-111
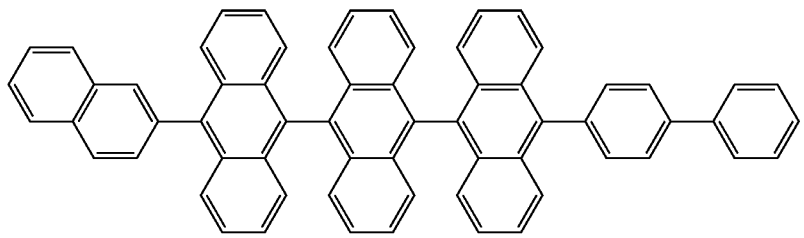
[Chem 17]
2a′-112
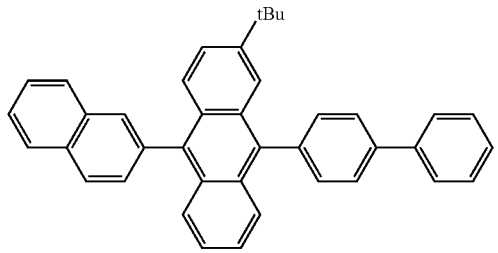
2a′-113
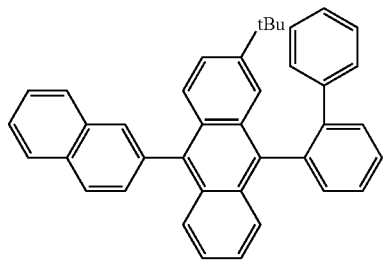
2a′-114
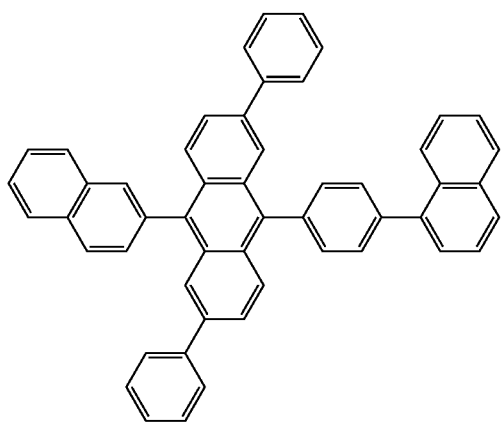
2a′-115
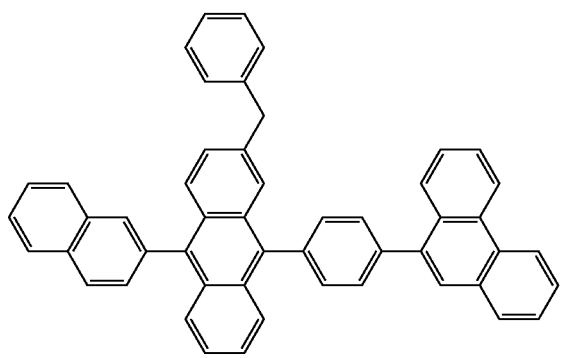

-continued
2a′-116
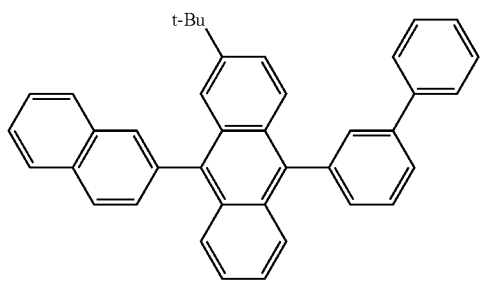
2a′-117
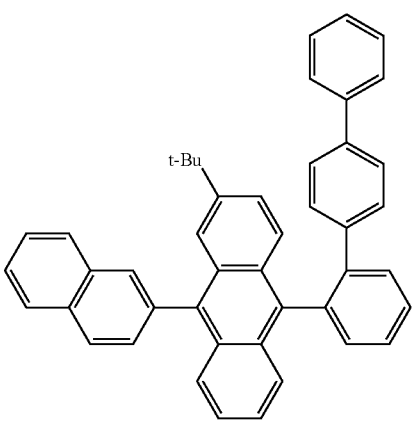
2a′-118
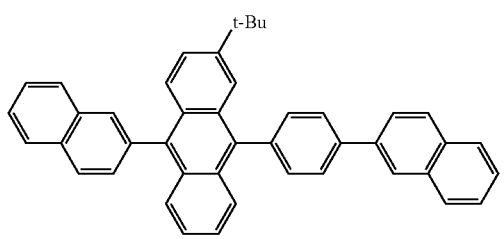
2a′-119
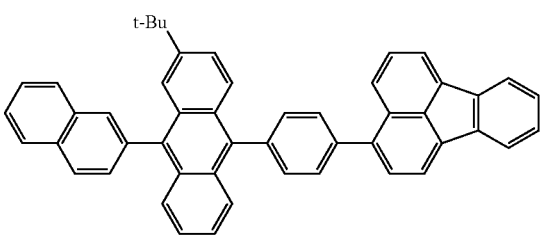
2a′-120
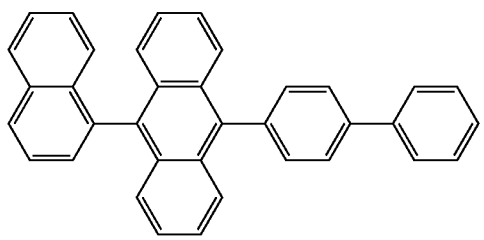
2a′-121
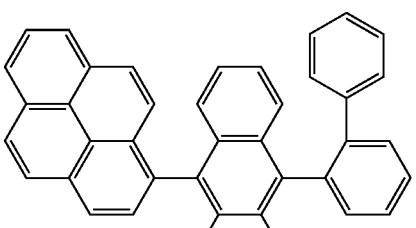
2a′-122
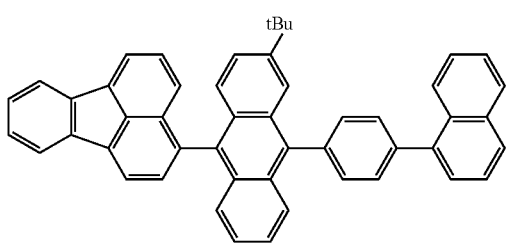
2a′-123
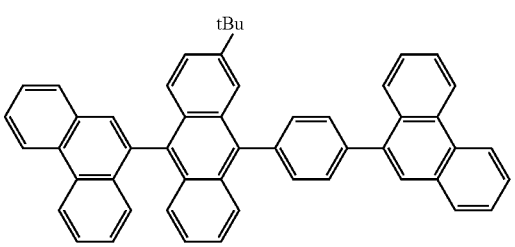
2a′-124
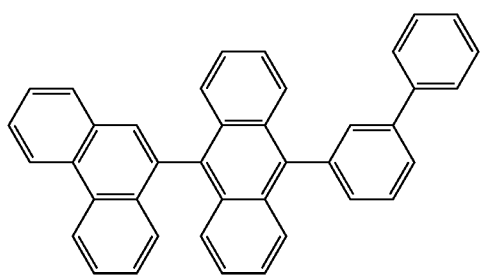
2a′-125
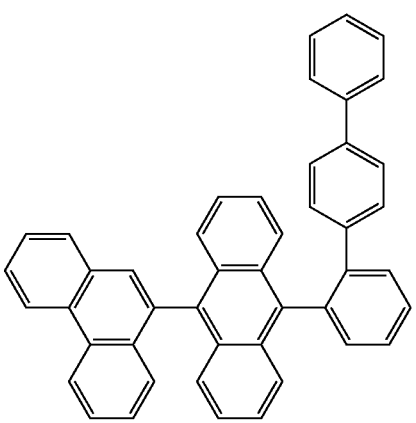

-continued
2a'-126
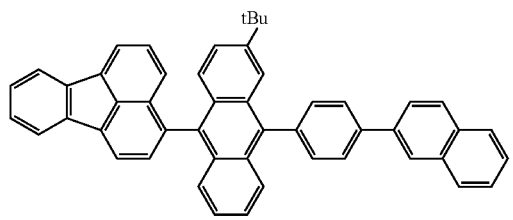
2a'-127
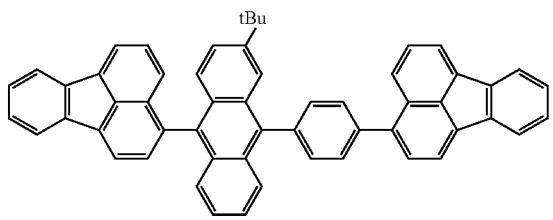
[Chem 18]
2a'-128
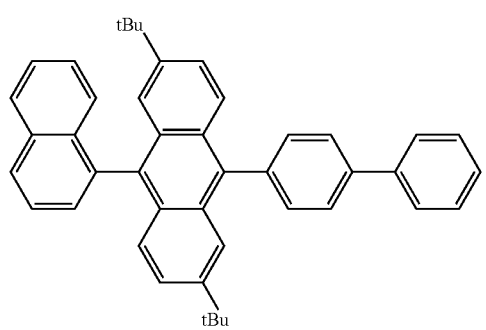
2a'-129
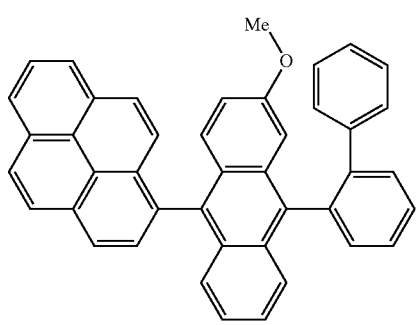
2a'-130
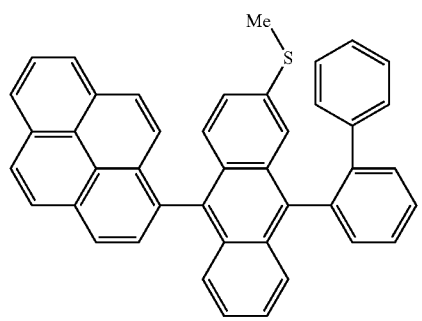
2a'-131
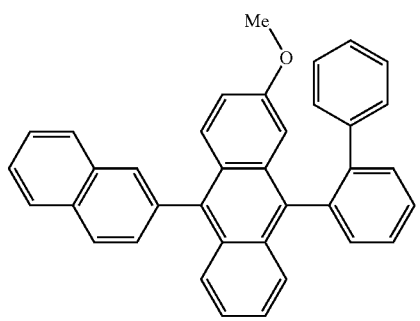
2a'-132
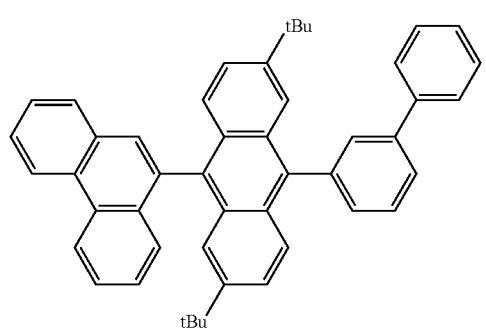
2a'-133
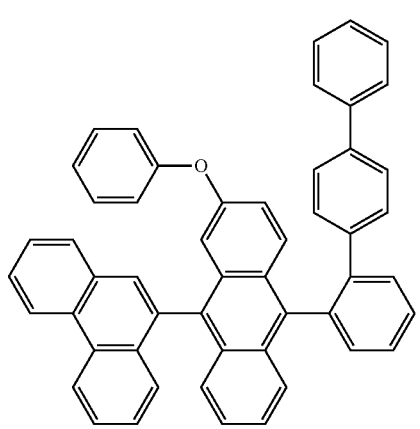

-continued
2a'-134
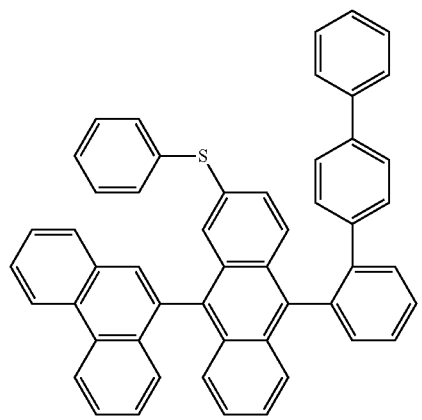
2a'-135
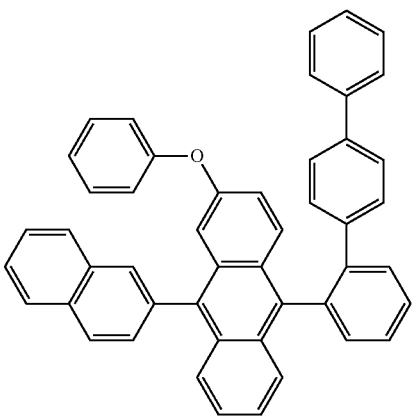
2a'-136
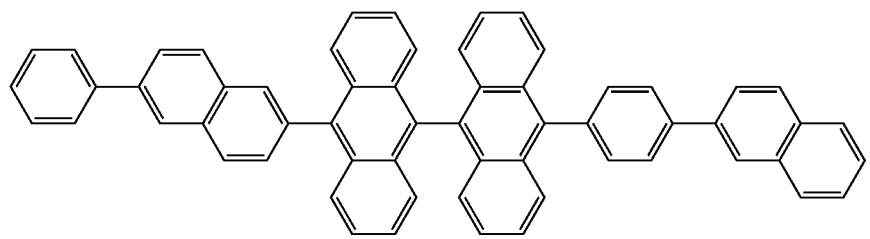
2a'-137
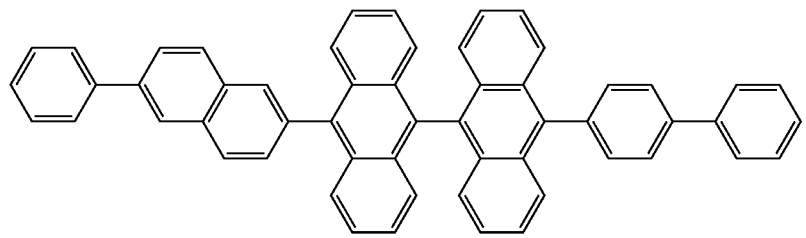
2a'-138
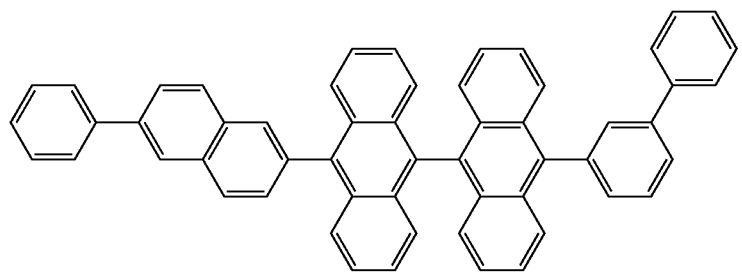
2a'-139
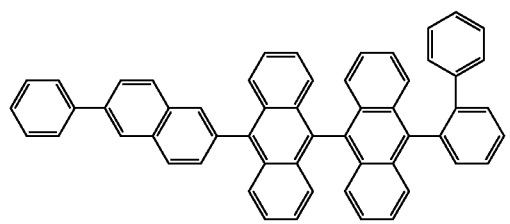
2a'-140
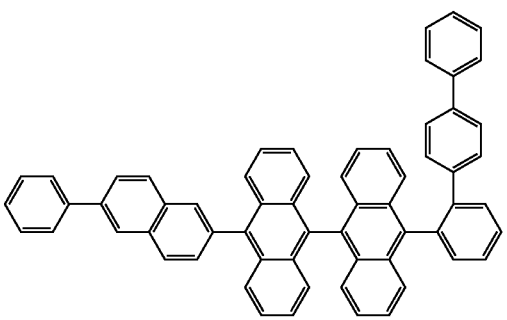

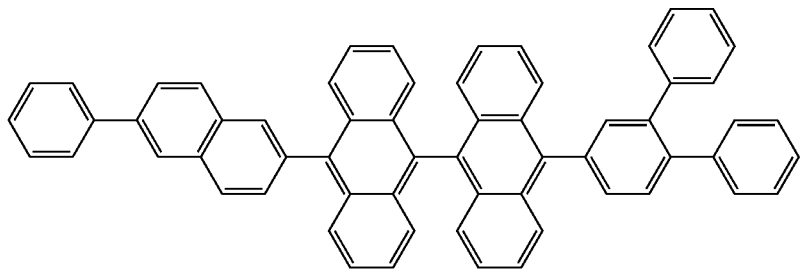
2a'-141
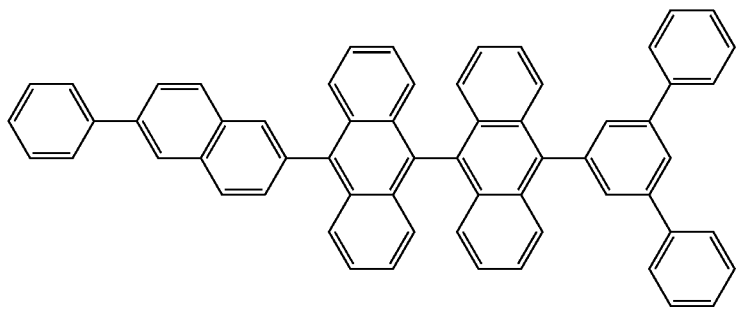
2a'-142
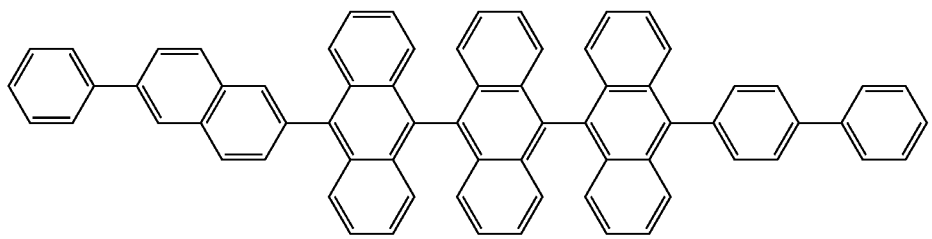
2a'-143
Specific examples of the pyrene derivative represented by the general formula (ii) used in the organic EL device of the present invention are shown below. However, the derivative is not particularly limited to these exemplified compounds.
[Chem 19]
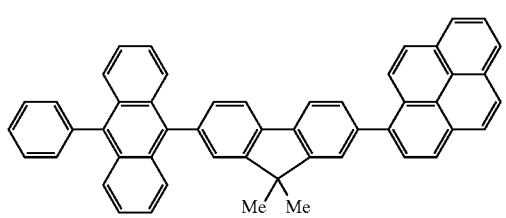
P1
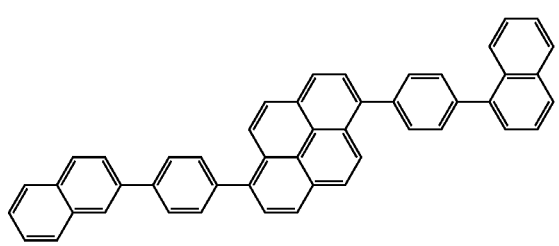
P2
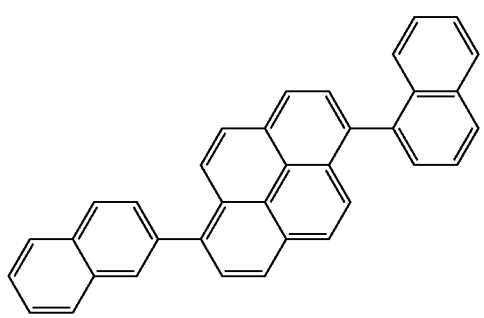
P3

P4
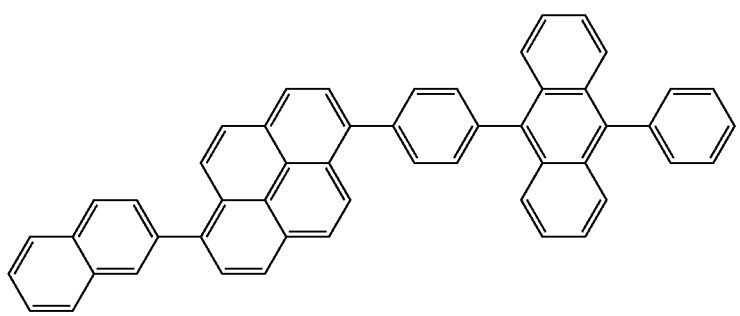
P5
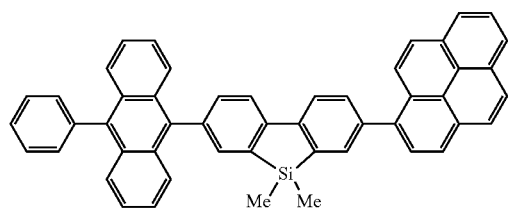
P6
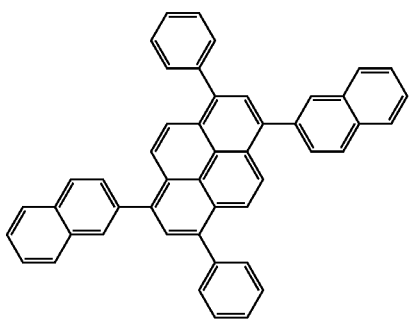
P7
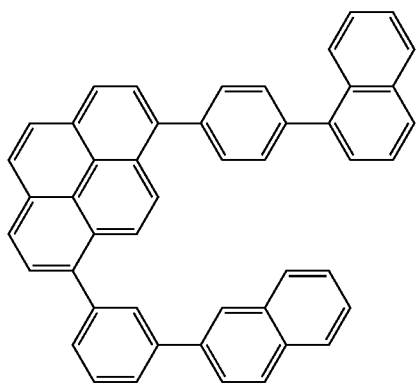
P8
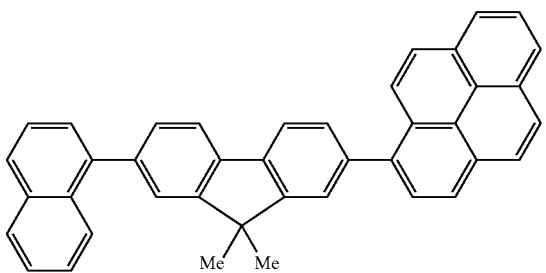
P9
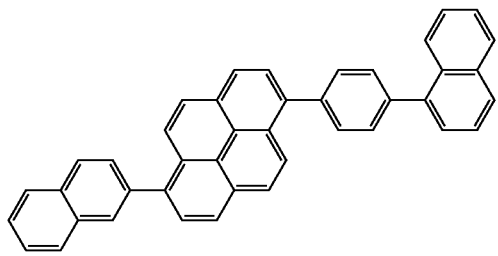
P10
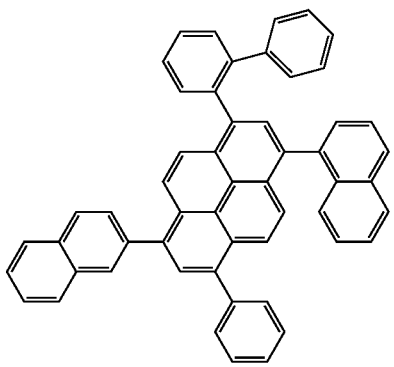

[Chem 20]
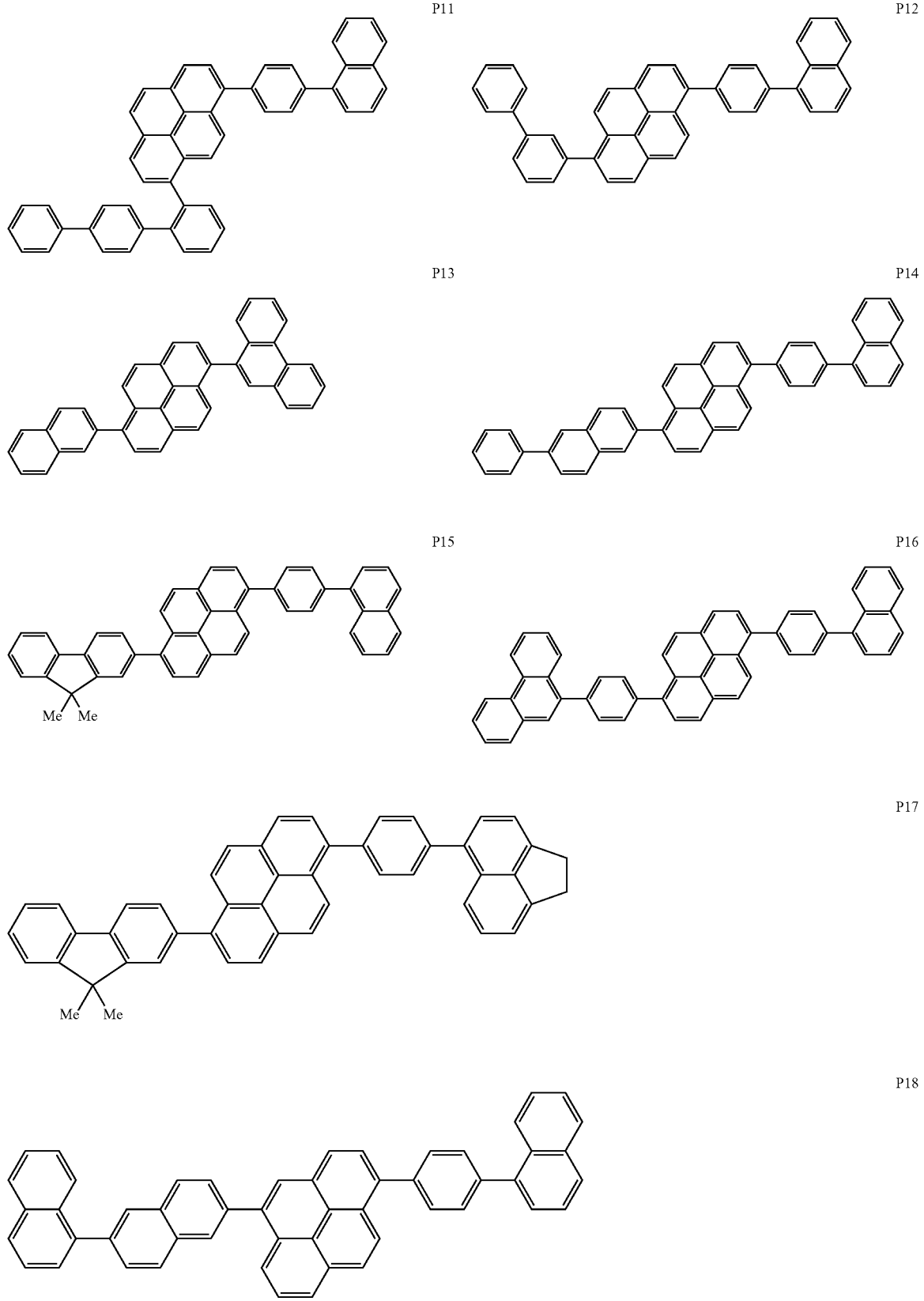

-continued

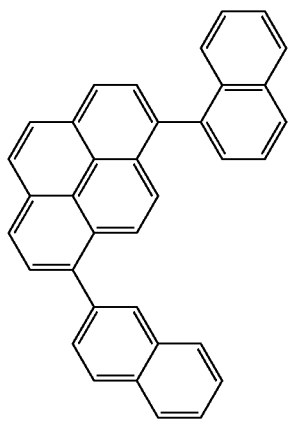
P19

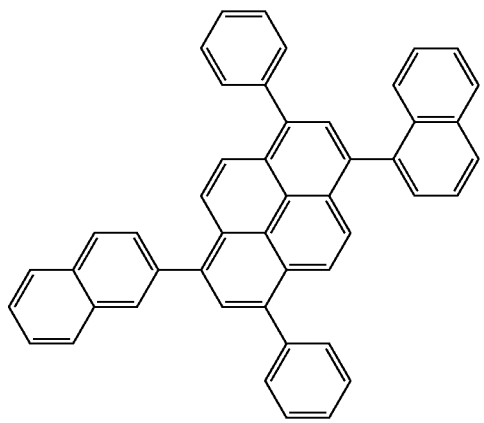
P20

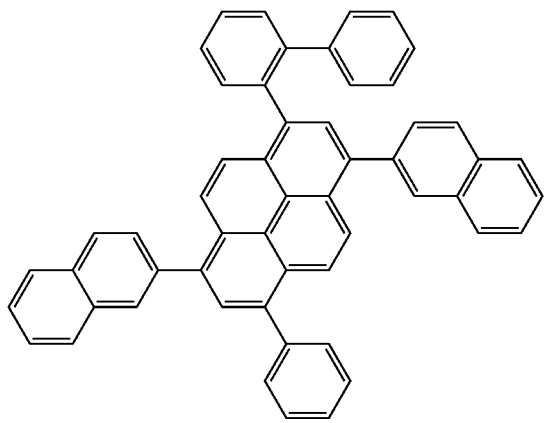
P21

In the present invention, the organic EL device having multiple organic thin film layers is a laminate having, for example, an (anode/hole injecting layer/light emitting layer/cathode), (anode/light emitting layer/electron injecting layer/cathode), or (anode/hole injecting layer/light emitting layer/electron injecting layer/cathode) constitution. When the organic EL device has a constitution of the multiple organic thin film layers, a reduction in luminance or lifetime due to quenching can be prevented. If needed, in addition to the aromatic diamine derivative of the present invention, a known light emitting material, doping material, hole injecting material, and electron injecting material can be used in combination in the multiple layers. Using a doping material in combination, improvements in emission luminance and luminous efficiency, and red or blue light emission can also be obtained.

In addition, each of the hole injecting layer, the light emitting layer, and the electron injecting layer may be formed of a layer constitution having two or more layers. At that time, in the case of the hole injecting layer, a layer for injecting a hole from the electrode is referred to as a hole injecting layer, and a layer for receiving the hole from the hole injecting layer and transporting the hole to the light emitting layer is referred to as a hole transporting layer. In the same manner, in the case of the electron injecting layer, a layer for injecting an electron from the electrode is referred to as an electron injecting layer, and a layer for receiving the electron from the electron injecting layer and transporting the electron to the light emitting layer is referred to as an electron transporting layer. Each of those layers is selected and used depending on factors such as the energy level of a material, heat resistance, and adhesiveness between the layer and an organic layer or a metal electrode.

Examples of a host material or a doping material other than those represented by the above general formulae (i) and (ii) which can be used in the light emitting layer together with the aromatic diamine derivative of the present invention include a known material including: polyfused aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene, 9,10-diphenylanthracene, 9,10-bis(phenylethinyl)anthracene, and 1,4-bis(9'-ethinylanthracene)benzene and derivatives thereof; organic metal complexes such as tris(8-quinolinolato)aluminum and bis-(2-methyl-8-quinolinolato)-4-(phenylphenolato)aluminum; a triarylamine derivative; a styrylamine derivative; a stilbene derivative; a coumarin derivative; a pyrane derivative; an oxazone derivative; a benzothiazole derivative; a benzoxazole derivative; a benzimidazole derivative; a pyrazine derivative; a cinnamate derivative; a diketopyrrolopyrrole derivative; an acridone derivative; and a quinacridone derivative, but the material is not limited thereto.

A compound having an ability of transporting a hole, having a hole injection effect from an anode and an excellent hole injection effect to a light emitting layer or a light emitting material, having an ability of preventing the migration of an exciton generated in the light emitting layer to an electron injecting layer or an electron injecting material, and having excellent thin film-formability is preferred as a hole injecting material. Specific examples of the compound include, but are not limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer.

Of the hole injecting materials that can be used in the organic EL device of the present invention, more effective hole injecting materials are an aromatic tertiary amine derivative and a phthalocyanine derivative.

Examples of the aromatic tertiary amine derivative include, but are not limited to, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenyl-cyclohexane, and an oligomer or a polymer having one of the aromatic tertiary amine skeletons.

Examples of the phthalocyanine (Pc) derivative include, but are not limited to, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O—GaPc, and naphthalocyanine derivatives.

In addition, the organic EL device of the present invention is preferably formed of a layer containing each of those aromatic tertiary amine derivatives and/or each of phthalocyanine derivatives, for example, the hole transporting layer or the hole injecting layer between a light emitting layer and an anode.

A compound having an ability of transporting electrons, having an electron injection effect from a cathode and an excellent electron injection effect to a light emitting layer or a light emitting material, having an ability of preventing the migration of an exciton generated in the light emitting layer to the hole injecting layer, and having excellent thin film-formability is preferred as an electron injecting material. Specific examples of the compound include fluorenone, anthraquinodimethane, diphenoquinone, thiopyranedioxide, oxazole, oxadiazole, triazole, imidazole, perylenetetracarboxylic acid, fluorenylidenemethane, anthraquinodimethane, anthrone, and derivatives thereof, but the compound is not limited thereto. In addition, an electron-accepting substance can be added to the hole injecting material or an electron-donating substance can be added to the electron injecting material to thereby sensitize the hole injecting material or the electron injecting material, respectively.

In the organic EL device of the present invention, more effective electron injecting materials are a metal complex compound and a nitrogen-containing five-membered ring derivative.

Examples of the metal complex compound include, but are not limited to, 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato) aluminum, tris(2-methyl-8-hydroxyquinolinato)aluminum, tris(8-hydroxyquinolinato)gallium, bis(10-hydroxybenzo[h] quinolinato)beryllium, bis(10-hydroxybenzo[h]quinolinato) zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium.

Examples of the nitrogen-containing five-membered derivative preferably include, an oxazole derivative, a thiazole derivative, an oxadiazole derivative, a thiadiazole derivative, and a triazole derivative. Specific examples of the derivative include, but are not limited to, 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene.

In the organic EL device of the present invention, in addition to the aromatic diamine derivatives represented by the general formula (I), at least one kind of known light emitting material, doping material, hole injecting material, and electron injecting material may be incorporated into the light emitting layers. In addition, the surface of the organic EL device obtained according to the present invention can be provided with a protective layer, or the entire device can be protected with silicone oil, a resin, or the like with a view to improving the stability of the device against temperature, humidity, an atmosphere, or the like.

A conductive material having a work function larger than 4 eV is suitably used in the anode of the organic EL device of the present invention. Examples of the conductive material to be used include: carbon, aluminum, vanadium, iron, cobalt, nickel, tungsten, silver, gold, platinum, palladium, and alloys thereof; metal oxides such as tin oxide and indium oxide to be used in an ITO substrate and an NESA substrate; and further, organic conductive resins such as polythiophene and polypyrrole. A conductive substance having a work function smaller than 4 eV is suitably used in the cathode. Examples of the conductive substance to be used include, but are not limited to, magnesium, calcium, tin, lead, titanium, yttrium, lithium, ruthenium, manganese, aluminum, lithium fluoride, and alloys thereof. Representative examples of the alloys include, but are not limited to, a magnesium/silver alloy, a magnesium/indium alloy, and a lithium/aluminum alloy. A ratio between the components of the alloy is controlled depending on, for example, the temperature of a deposition source, an atmosphere, and the degree of vacuum, and is selected appropriately. Each of the anode and the cathode may be formed in a layer constitution having two or more layers if needed.

It is desirable that at least one surface of the organic EL device of the present invention is sufficiently transparent in the emission wavelength region of the device so that the device can efficiently emit light. A substrate is also desirably transparent. A transparent electrode is formed by using any one of the above conductive materials, and is set by a method such as deposition or sputtering in such a manner that desired translucency is secured. The light transmittance of an electrode on a light emitting surface is desirably 10% or more. The substrate is not limited as long as it has mechanical strength, thermal strength, and transparency. Examples of the substrate include a glass substrate and a transparent resin film. Examples of the transparent resin film include, but are not limited to, polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyether imide, polyimide, and polypropylene.

Any one of dry film forming methods such as vacuum deposition, sputtering, plasma, and ion plating, and wet film forming methods such as spin coating, dipping, and flow coating is applicable to the formation of each layer of the organic EL device according to the present invention. The thickness of each layer is not particularly limited, but must be set to an appropriate thickness. An excessively large thickness requires an increased applied voltage for obtaining certain optical output, resulting in poor efficiency. An excessively small thickness causes a pin hole or the like, with the result that sufficient emission luminance cannot be obtained even when an electric field is applied. In general, the thickness is in the range of preferably 5 nm to 10 µm, or more preferably 10 nm to 0.2 µm.

In the case of a wet film forming method, a material of which each layer is formed is dissolved or dispersed into an appropriate solvent such as ethanol, chloroform, tetrahydrofuran, or dioxane, to thereby form a thin film. At that time, any one of the above solvents may be used. In addition, an appropriate resin or additive may be used in each of the organic thin film layers for, for example, improving film formability or preventing a pin hole in the layer. Examples of an available resin include: insulating resins such as polystyrene, polycarbonate, polyallylate, polyester, polyamide, polyurethane, polysulfone, polymethyl methacrylate, polymethyl acrylate, and cellulose, and copolymers thereof; photoconductive resins such as poly-N-vinylcarbazole and polysilane; and conductive resins such as polythiophene and polypyrrole. Examples of the additive include an antioxidant, a UV absorber, and a plasticizer.

The organic EL device of the present invention can find use in applications including a flat luminous body such as the flat panel display of a wall hanging television, a light source for the backlight, meters, or the like of a copying machine, a printer, or a liquid crystal display, a display panel, and a signal lamp. In addition, the material of the present invention can be used in not only the field of an organic EL device but also the fields of an electrophotographic photosensitive member, a photoelectric conversion device, a solar cell, an image sensor, and the like.

EXAMPLES

Next, the present invention is described in more detail by way of examples. However, the present invention is by no means limited by these examples.

Synthesis Example 1

Synthesis of Compound (D-1)

In a stream of argon, 3.8 g (10 mmol) of 6,12-dibromochrysene, 6.4 g (25 mmol) of N-[4-(trimethylsilyl)phenyl]-N-p-tolylamine, 0.03 g (1.5 mol %) of palladium acetate, 0.06 g (3 mol %) of tri-t-butylphosphine, 2.4 g (25 mmol) of sodium t-butoxide, and 100 mL of dry toluene were loaded into a 300-mL three-necked flask with a cooling tube, and the mixture was stirred under heating at 100° C. overnight. After the completion of the reaction, the precipitated crystal was taken by filtration, and was then washed with 50 mL of toluene and 100 mL of methanol. Thus, 6.0 g of a pale yellow powder were obtained. The resultant powder was identified as Compound (D-1) described above because field desorption mass spectrometry (FD-MS) confirmed that the powder had a ratio m/e of 734.

Synthesis Example 2

Synthesis of Compound (D-2)

Synthesis was performed in the same manner as in Synthesis Example 1 except that N-[4-(trimethylsilyl)phenyl]-N-4-ethylphenylamine was used instead of N-[4-(trimethylsilyl)phenyl]-N-p-tolylamine in Synthesis Example 1. The resultant powder was identified as Compound (D-2) described above because FD-MS confirmed that the powder had a ratio m/e of 762.

Synthesis Example 3

Synthesis of Compound (D-3)

Synthesis was performed in the same manner as in Synthesis Example 1 except that N-[4-(trimethylsilyl)phenyl]-N-4-isopropylphenylamine was used instead of N-[4-(trimethylsilyl)phenyl]-N-p-tolylamine in Synthesis Example 1. The resultant powder was identified as Compound (D-3) described above because FD-MS confirmed that the powder had a ratio m/e of 790.

Synthesis Example 4

Synthesis of Compound (D-4)

Synthesis was performed in the same manner as in Synthesis Example 1 except that N-[4-(trimethylsilyl)phenyl]-N-4-t-butylphenylamine was used instead of N-[4-(trimethylsilyl)phenyl]-N-p-tolylamine in Synthesis Example 1. The resultant powder was identified as Compound (D-4) described above because FD-MS confirmed that the powder had a ratio m/e of 818.

Synthesis Example 5

Synthesis of Compound (D-5)

Synthesis was performed in the same manner as in Synthesis Example 1 except that N-[4-(trimethylsilyl)phenyl]-N-2,4-dimethylphenylamine was used instead of N-[4-(trimethylsilyl)phenyl]-N-p-tolylamine in Synthesis Example 1. The resultant powder was identified as Compound (D-5) described above because FD-MS confirmed that the powder had a ratio m/e of 762.

Synthesis Example 6

Synthesis of Compound (D-6)

Synthesis was performed in the same manner as in Synthesis Example 1 except that N-[4-(trimethylsilyl)phenyl]-N-3,4-dimethylphenylamine was used instead of N-[4-(trimethylsilyl)phenyl]-N-p-tolylamine in Synthesis Example 1. The resultant powder was identified as Compound (D-6) described above because FD-MS confirmed that the powder had a ratio m/e of 762.

Synthesis Example 7

Synthesis of Compound (D-7)

Synthesis was performed in the same manner as in Synthesis Example 1 except that N-[4-(trimethylsilyl)phenyl]-N-3, 5-diethylphenylamine was used instead of N-[4-(trimethylsilyl)phenyl]-N-p-tolylamine in Synthesis Example 1. The resultant powder was identified as Compound (D-7) described above because FD-MS confirmed that the powder had a ratio m/e of 818.

Synthesis Example 8

Synthesis of Compound (D-8)

Synthesis was performed in the same manner as in Synthesis Example 1 except that N-[4-(trimethylsilyl)phenyl]-N-3,4,5-trimethylphenylamine was used instead of N-[4-(trimethylsilyl)phenyl]-N-p-tolylamine in Synthesis Example 1. The resultant powder was identified as Compound (D-8) described above because FD-MS confirmed that the powder had a ratio m/e of 790.

Synthesis Example 9

Synthesis of Compound (D-9)

Synthesis was performed in the same manner as in Synthesis Example 1 except that N-[4-(trimethylsilyl)phenyl]-N-m-trylamine was used instead of N-[4-(trimethylsilyl)phenyl]-N-p-tolylamine in Synthesis Example 1. The resultant powder was identified as Compound (D-9) described above because FD-MS confirmed that the powder had a ratio m/e of 734.

Synthesis Example 10

Synthesis of Compound (D-10)

Synthesis was performed in the same manner as in Synthesis Example 1 except that N-[4-(trimethylsilyl)phenyl]-N-3-t-butylphenylamine was used instead of N-[4-(trimethylsilyl)phenyl]-N-p-tolylamine in Synthesis Example 1. The resultant powder was identified as Compound (D-10) described above because FD-MS confirmed that the powder had a ratio m/e of 818.

Synthesis Example 11

Synthesis of Compound (D-11)

Synthesis was performed in the same manner as in Synthesis Example 1 except that N-[4-(trimethylsilyl)phenyl]-N-o-tolylamine was used instead of N-[4-(trimethylsilyl)phenyl]-N-p-tolylamine in Synthesis Example 1. The resultant powder was identified as Compound (D-11) described above because FD-MS confirmed that the powder had a ratio m/e of 734.

Synthesis Example 12

Synthesis of Compound (D-12)

Synthesis was performed in the same manner as in Synthesis Example 1 except that N-[4-(trimethylsilyl)phenyl]-N-4-methoxyphenylamine was used instead of N-[4-(trimethylsilyl)phenyl]-N-p-tolylamine in Synthesis Example 1. The resultant powder was identified as Compound (D-12) described above because FD-MS confirmed that the powder had a ratio m/e of 766.

Synthesis Example 13

Synthesis of Compound (D-13)

Synthesis was performed in the same manner as in Synthesis Example 1 except that N-[4-(trimethylsilyl)phenyl]-N-4-cyclohexylphenylamine was used instead of N-[4-(trimethylsilyl)phenyl]-N-p-tolylamine in Synthesis Example 1. The resultant powder was identified as Compound (D-13) described above because FD-MS confirmed that the powder had a ratio m/e of 870.

Synthesis Example 14

Synthesis of Compound (D-14)

Synthesis was performed in the same manner as in Synthesis Example 1 except that N-[4-(trimethylsilyl)phenyl]-N-4-cyclopentylphenylamine was used instead of N-[4-(trimethylsilyl)phenyl]-N-p-tolylamine in Synthesis Example 1. The resultant powder was identified as Compound (D-14) described above because FD-MS confirmed that the powder had a ratio m/e of 842.

Synthesis Example 15

Synthesis of Compound (D-15)

Synthesis was performed in the same manner as in Synthesis Example 1 except that N-[4-(trimethylsilyl) phenyl]-N-5-(2,3-dihydro-1H-indenyl)amine was used instead of N-[4-(trimethylsilyl) phenyl]-N-p-tolylamine in Synthesis Example 1. The resultant powder was identified as Compound (D-15) described above because FD-MS confirmed that the powder had a ratio m/e of 786.

Example 1

A transparent electrode formed of indium tin oxide and having a thickness of 120 nm was provided on a glass substrate measuring 25 mm by 75 mm by 1.1 mm. The glass substrate was subjected to UV/ozone irradiation, and washed. After that, the substrate was placed in a vacuum deposition apparatus.

First, N',N''-bis[4-(diphenylamino)phenyl]-N',N'''-diphenylbiphenyl-4,4'-diamine was deposited from the vapor so as to serve as a hole injecting layer having a thickness of 60 nm. After that, N,N,N',N'-tetrakis(4-biphenyl)-4,4'-benzidine was deposited from the vapor onto the layer so as to serve as a hole transporting layer having a thickness of 20 nm. Next, 10-(4-(naphthalene-1-yl)phenyl-9-(naphthalene-2-yl) anthracene and Compound (D-1) described above were simultaneously deposited from the vapor at a mass ratio of 40:2 so that a light emitting layer having a thickness of 40 nm might be formed.

Next, tris(8-hydroxyquinolinato) aluminum was deposited from the vapor onto the light emitting layer so as to serve as an electron injecting layer having a thickness of 20 nm. Then, lithium fluoride was deposited from the vapor so as to have a thickness of 1 nm, and then aluminum was deposited from the vapor so as to have a thickness of 150 nm. The aluminum/lithium fluoride functions as a cathode. Thus, an organic EL device was produced.

The resultant device was then subjected to an energization test. As a result, pure blue light emission having a current efficiency of 3.0 cd/A and a luminance of 490 cd/m$^2$ (luminous maximum wavelength: 457 nm) was obtained at a voltage of 6.5 V and a current density of 10 mA/m². A continuous DC energization test was performed at initial luminance of 500 cd/m². As a result, a half lifetime was 2500 hours.

Example 2

An organic EL device was produced in the same manner as in Example 1 except that Compound (D-2) was used as a doping material instead of Compound (D-1) in Example 1.

The resultant organic EL device was subjected to an energization test. As a result, pure blue light emission having a luminance of 500 cd/m² (luminous wavelength: 457 nm) was obtained at a voltage of 6.5 V and a current density of 10 mA/m². In addition, a continuous energization test was performed in the same manner as in Example 1. As a result, a half lifetime was 2200 hours.

Example 3

An organic EL device was produced in the same manner as in Example 1 except that Compound (D-3) was used as a doping material instead of Compound (D-1) in Example 1.

The resultant organic EL device was subjected to an energization test. As a result, pure blue light emission having a luminance of 500 cd/m² (luminous wavelength: 457 nm) was obtained at a voltage of 6.5 V and a current density of 10 mA/m². In addition, a continuous energization test was performed in the same manner as in Example 1. As a result, a half lifetime was 2300 hours.

Comparative Example 1

An organic EL device was produced in the same manner as in Example 1 except that 6,12-N,N'-[tetrakis (4-trimethylsilylphenyl] diaminochrysene was used as a doping material instead of Compound (D-1) in Example 1.

The resultant organic EL device was subjected to an energization test. As a result, pure blue light emission having a luminance of 300 cd/m² (luminous wavelength: 452 nm) was obtained at a voltage of 6.5 V and a current density of 10 mA/m². In addition, a continuous energization test was performed in the same manner as in Example 1. As a result, a half lifetime was 1500 hours.

The foregoing results show that the organic EL devices of Examples 1 to 3 each had improved current efficiency and an improved half lifetime as compared with those of Comparative Example 1 while maintaining pure blue light emission.

Industrial Applicability

The organic EL device using the aromatic diamine derivative of the present invention has high luminous efficiency, hardly deteriorates even after long-term use, and has a long lifetime. Therefore, the organic EL device is useful as a flat luminous body of a wall hanging television or a light source for backlight or the like of a display.

The invention claimed is:

1. An organic electroluminescence device, comprising an organic thin film layer formed of one or more layers including at least a light emitting layer and interposed between a cathode and an anode,
wherein the light emitting layer comprises at least one dopant and at least one host material,
wherein the at least one dopant is an aromatic diamine derivative by itself or as a component of a mixture, and the at least one host material is an anthracene derivative, wherein the aromatic diamine derivative is represented by formula (I):

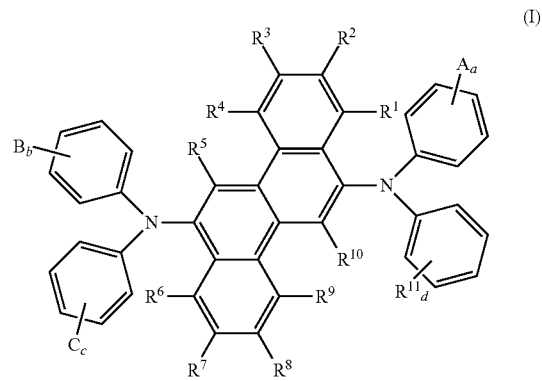

where:
$R^2$, $R^3$, $R^7$ and $R^8$ each represent a hydrogen atom, and $R^1$, $R^4$, $R^5$, $R^6$, $R^9$, and $R^{10}$ each independently represent a hydrogen atom, an alkyl group having 1 to 50 carbon atoms, a cycloalkyl group having 3 to 50 carbon atoms, an aralkyl group having 7 to 50 carbon atoms, or an aryl group having 6 to 50 carbon atoms, and $R^{11}$ represents a substituted or unsubstituted alkyl group having 1 to 10 carbon atoms;
wherein a plurality of $R^{11}$ groups, if present, are not bonded to each other and do not form a ring structure, and
A and C each represents a substituted or unsubstituted silyl group, and B represents a substituted or unsubstituted alkyl group having 1 to 10 carbon atoms, a, b, c, and d each independently represent an integer of 1 to 5, and when a, b, c, or d represents an integer of 2 to 5, A's, B's, C's, or $R^{11}$'s may represent groups identical to or different from each other on the same benzene ring,
and
wherein the anthracene derivative is represented by formula (i):

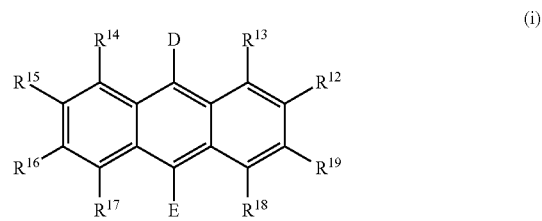

where $R^{12}$ to $R^{19}$ each independently represent a group selected from a hydrogen atom, a substituted or unsubstituted aryl group having 6 to 50 carbon atoms, a substituted or unsubstituted heteroaryl group having 4 to 50 carbon atoms, a substituted or unsubstituted alkyl group having 1 to 50 carbon atoms, a substituted or unsubstituted cycloalkyl group having 3 to 50 carbon atoms, a substituted or unsubstituted alkoxyl group having 1 to 50 carbon atoms, a substituted or unsubstituted aralkyl group whose aryl portion has 6 to 50 carbon atoms and whose alkyl portion has 1 to 50 carbon atoms, a substituted or unsubstituted aryloxy group having 5 to 50 carbon atoms, a substituted or unsubstituted arylthio group having 5 to 50 carbon atoms, a substituted or unsubstituted alkoxycarbonyl group having 1 to 50 carbon atoms, a substituted or unsubstituted silyl group, a carboxyl group, a halogen atom, a cyano group, a nitro group, and a hydroxyl group, and D represents a group derived from a substituted or unsubstituted aromatic ring having 6 to 20 carbon atoms; and E represents an optionally substituted group selected from the group consisting of 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 3-methyl-2naphthyl, 4-methyl-1naphthyl, and 4-methyl-1-anthryl.

2. The organic electroluminescence device according to claim 1, wherein, in the formula (I), the silyl group is a trialkylsilyl group, a dialkyl-monoarylsilyl group, a monoalkyl-diarylsilyl group, or a triarylsilyl group.

3. The organic electroluminescence device according to claim 1, wherein, in the formula (I), the silyl group is a trimethylsilyl group.

4. The organic electroluminescence device according to claim 1, wherein the aromatic diamine derivative is represented by any one of compounds represented by the following formulae:

D-1
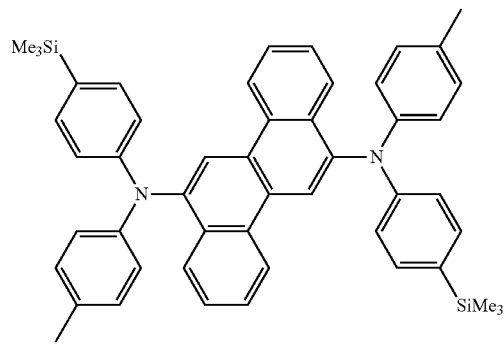

D-2
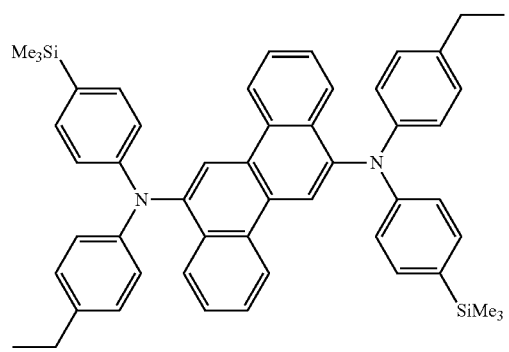

-continued

D-3
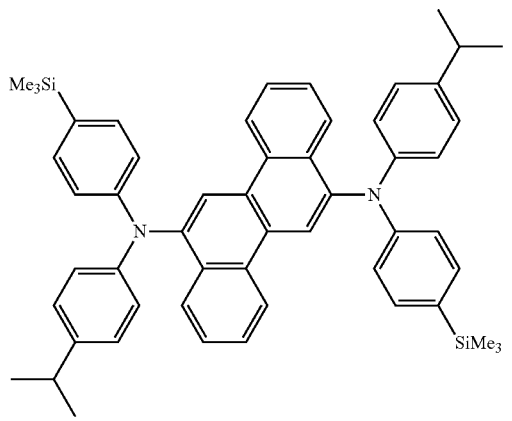

D-4
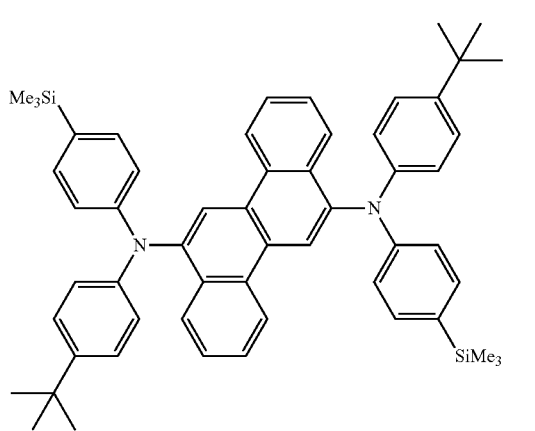

D-5
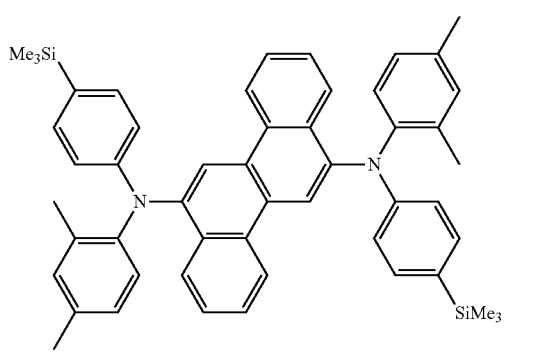

D-6
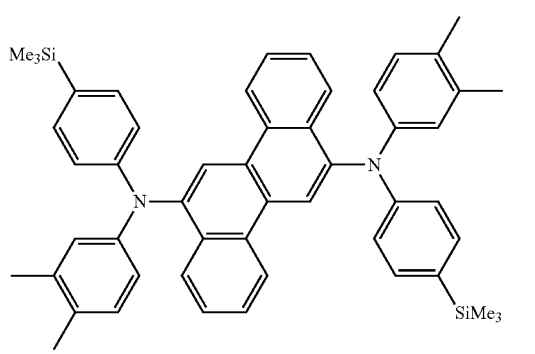

-continued

D-7
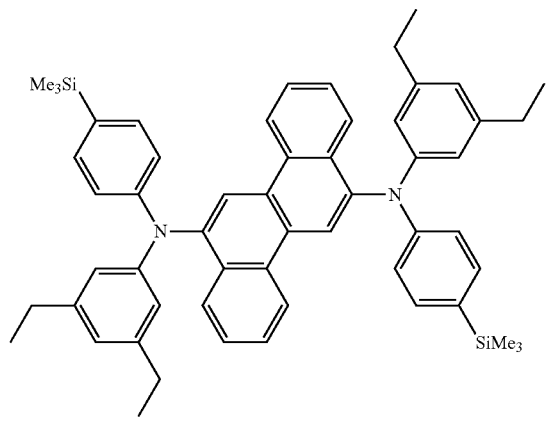

D-8
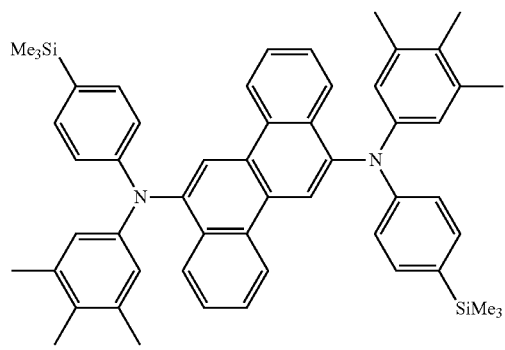

D-9
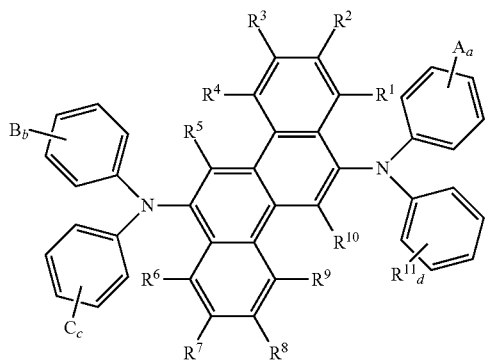

D-10
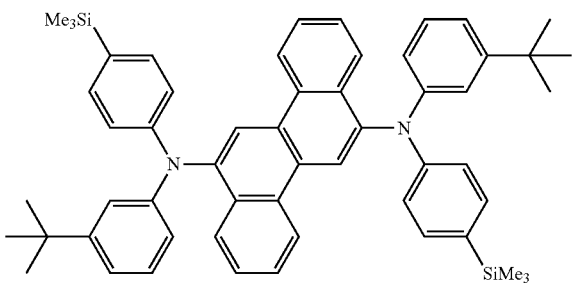

-continued

D-11
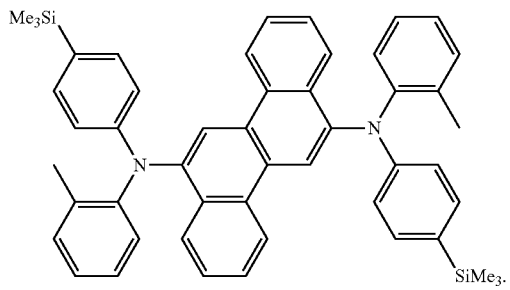

5. The organic electroluminescence device according to claim 1, wherein the aromatic diamine derivative is a light emitting material for an organic electroluminescence device.

6. The organic electroluminescence device according to claim 1, wherein the aromatic diamine derivative is a blue light emitting material for an organic electroluminescence device.

7. The organic electroluminescence device according to claim 1, wherein the aromatic diamine derivative is a doping material for an organic electroluminescence device.

8. An organic electroluminescence device, comprising an organic thin film layer formed of one or more layers including at least a light emitting layer and interposed between a cathode and an anode,
wherein the light emitting layer comprises at least one dopant and at least one host material,
wherein the at least one dopant is an aromatic diamine derivative by itself or as a component of a mixture, and the at least one host material is a pyrene derivative,
wherein the aromatic diamine derivative is represented by formula (I):

(I)
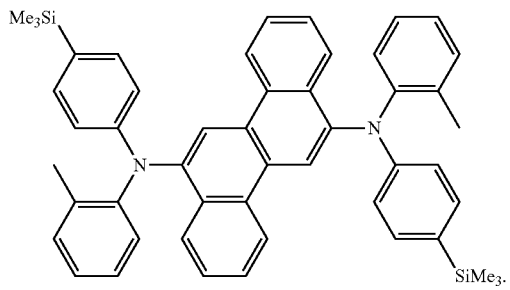

where:
$R^2$, $R^3$, $R^7$ and $R^8$ each represent a hydrogen atom, and $R^1$, $R^4$, $R^5$, $R^6$, $R^9$, and $R^{10}$ each independently represent a hydrogen atom, an alkyl group having 1 to 50 carbon atoms, a cycloalkyl group having 3 to 50 carbon atoms, an aralkyl group having 7 to 50 carbon atoms, or an aryl group having 6 to 50 carbon atoms, and $R^{11}$ represents a substituted or unsubstituted alkyl group having 1 to 10 carbon atoms; and
A and C each represents a substituted or unsubstituted silyl group, and B represents a substituted or unsubstituted alkyl group having 1 to 10 carbon atoms, a, b, c, and d each independently represent an integer of 1 to 5, and when a, b, c, or d represents an integer of 2 to 5, A's, B's, C's, or $R^{11}$'s may represent groups identical to or different from each other on the same benzene ring, and wherein the pyrene derivative is represented by formula (ii):

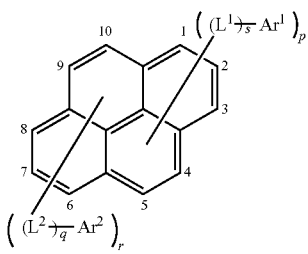

(ii)

where:

Ar$^1$ and Ar$^2$ each independently represent a substituted or unsubstituted aryl group having 6 to 50 carbon atoms;

L$^1$ and L$^2$ each independently represent a substituted or unsubstituted phenylene group, a substituted or unsubstituted naphthalenylene group, a substituted or unsubstituted fluorenylene group, or a substituted or unsubstituted dibenzosilolylene group;

s represents an integer of 0 to 2, p represents an integer of 1 to 4, q represents an integer of 0 to 2, and r represents an integer of 0 to 4; and L$^1$ or Ar$^1$ is bonded to any one of 1- to 5-positions of pyrene and L$^2$ or Ar$^2$ is bonded to any one of 6- to 10-positions of pyrene, provided that, when p+r is an even number, Ar$^1$, Ar$^2$, L$^1$, and L$^2$ satisfy the following condition (1) or (2):

(1) Ar$^1$≠Ar$^2$ and/or L$^1$≠L$^2$ where ≠ means that groups on both of its sides are different from each other in structure; or (2) when Ar$^1$=Ar$^2$ and L$^1$=L$^2$, (2-1) s≠q and/or p≠r, or (2-2) if s=q and p=r, (2-2-1) L$^1$ and L$^2$ are, or pyrene is, bonded to different bonding positions on Ar$^1$ and Ar$^2$, or (2-2-2) in a case where L$^1$ and L$^2$ are, or pyrene is, bonded to the same bonding positions on Ar$^1$ and Ar$^2$, substitution positions of L$^1$ and L$^2$ or Ar$^1$ and Ar$^2$ on pyrene exclude 1- and 6-positions or 2- and 7-positions.

9. The organic electroluminescence device according to claim 1, wherein, in the formula (I), $R^{11}$ and B each represents a methyl group, an ethyl group, an n-propyl group, an isopropyl group, an n-butyl group, an isobutyl group, an s-butyl group, a t-butyl group or a pentyl group.

10. The organic electroluminescence device according to claim 1, wherein, in the formula (I), $R^{11}$ and B each represents a methyl group, an ethyl group, an isopropyl group or a t-butyl group.

* * * * *